US009284252B2

(12) United States Patent
Herzberg et al.

(10) Patent No.: US 9,284,252 B2
(45) Date of Patent: Mar. 15, 2016

(54) USE OF JASMONATE ESTER DERIVATIVES FOR TREATING BENIGN HYPERPROLIFERATIVE SKIN DISORDERS

(71) Applicant: SEPAL PHARMA LTD., Sitrya (IL)

(72) Inventors: Max Herzberg, Sitrya (IL); Frederic Revah, Paris (FR)

(73) Assignee: SEPAL PHARMA LTD., Sitrya (IL)

( * ) Notice: Subject to any disclaimer, the term of this patent is extended or adjusted under 35 U.S.C. 154(b) by 0 days.

(21) Appl. No.: 14/497,020

(22) Filed: Sep. 25, 2014

(65) Prior Publication Data

US 2015/0080430 A1   Mar. 19, 2015

Related U.S. Application Data

(63) Continuation-in-part of application No. 13/376,917, filed as application No. PCT/IL2010/000438 on Jun. 3, 2010, now abandoned.

(60) Provisional application No. 61/185,221, filed on Jun. 9, 2009, provisional application No. 61/249,265, filed on Oct. 7, 2009.

(51) Int. Cl.
*C07D 215/24* (2006.01)
*C07C 57/26* (2006.01)

(52) U.S. Cl.
CPC .............. *C07C 57/26* (2013.01); *C07D 215/24* (2013.01)

(58) Field of Classification Search
CPC .................................................... C07D 215/24
See application file for complete search history.

(56) References Cited

U.S. PATENT DOCUMENTS

| | | | |
|---|---|---|---|
| 3,932,389 | A | 1/1976 | Johnson |
| 3,951,876 | A | 4/1976 | Celli |
| 3,981,891 | A | 9/1976 | Celli |
| 4,154,949 | A | 5/1979 | Bindra |
| 5,476,945 | A | 12/1995 | Ikegawa |
| 5,637,484 | A | 6/1997 | Yukimune |
| 5,652,266 | A | 7/1997 | Bobier-Rival |
| 5,733,535 | A | 3/1998 | Hollingshead |
| 5,854,067 | A | 12/1998 | Newgard |
| 5,891,717 | A | 4/1999 | Newgard |
| 6,140,067 | A | 10/2000 | Anderson |
| 6,187,946 | B1 | 2/2001 | Fujisawa |
| 6,469,061 | B1 | 10/2002 | Flescher |
| 6,689,339 | B1 | 2/2004 | Tanaka |
| 6,861,431 | B2 | 3/2005 | Gudkov |
| 7,402,602 | B2 | 7/2008 | Bigg |
| 8,247,439 | B2 | 8/2012 | Herzberg |
| 8,481,594 | B2 | 7/2013 | Boulle |
| 2003/0219461 | A1 | 11/2003 | Britten |
| 2003/0224024 | A1 | 12/2003 | Leveque |
| 2004/0029839 | A1 | 2/2004 | Boulle |
| 2004/0081673 | A1 | 4/2004 | Rayner |
| 2004/0091493 | A1 | 5/2004 | Perrier |
| 2004/0116356 | A1 | 6/2004 | Malik |
| 2004/0116511 | A1 | 6/2004 | Malik |
| 2004/0180380 | A1 | 9/2004 | Lee |
| 2004/0259906 | A1 | 12/2004 | Altiok |
| 2005/0288210 | A1 | 12/2005 | Monteleone |
| 2006/0057558 | A1 | 3/2006 | Scott |
| 2006/0134237 | A1 | 6/2006 | Greene |
| 2006/0148732 | A1 | 7/2006 | Gutterman |
| 2007/0082852 | A1 | 4/2007 | Malik |
| 2008/0254055 | A1 | 10/2008 | Oblong |
| 2009/0064349 | A1 | 3/2009 | Goldstein |
| 2009/0197927 | A1 | 8/2009 | Herzberg |
| 2009/0197939 | A1 | 8/2009 | Walke |
| 2009/0252697 | A1 | 10/2009 | Barbarat |
| 2010/0069497 | A1 | 3/2010 | Boulle |
| 2011/0245134 | A1 | 10/2011 | Smets |
| 2011/0245136 | A1 | 10/2011 | Smets |

FOREIGN PATENT DOCUMENTS

| | | |
|---|---|---|
| CN | 1470494 | 1/2004 |
| CN | 102726514 | 10/2012 |
| DE | 202012000163 | 1/2012 |
| EP | 0585104 | 3/1994 |
| EP | 0683232 | 11/1995 |
| EP | 1333021 | 8/2003 |
| FR | 2863893 | 6/2005 |
| FR | 2877222 | 5/2006 |
| GB | 1508169 | 4/1978 |
| JP | 63-122669 | 5/1988 |

(Continued)

OTHER PUBLICATIONS

Reischer-Pelech and Flescher (2012) Jasmonates: Plant Stress Hormones as Anticancer Agents. In: Emerging Trends in Dietary Components for Preventing and Combating Disease. Patil BS, Jayaprakasha GK, Murthy KNC, Seeram NP (Editors), ACS Symp Ser, Amer Chemical Society, Washington USA, pp. 303-322.
Robey and Hay (2006) Mitochondrial hexokinases, novel mediators of the antiapoptotic effects of growth factors and Akt. Oncogene 25 (34): 4683-96.
Rotem et al., (2003) The anticancer agent methyl jasmonate induces activation of stress-regulated c-Jun N-terminal kinase and p38 protein kinase in human lymphoid cells. Leukemia 17(11): 2230-56.
Rotem et al., (2005) Jasmonates: Novel anticancer agents acting directly and selectively on human cancer cell mitochondria. Cancer Res 65 (5): 1984-93.
Saniewski et al., (1987) The effect of methyl jasmonate on ethylene and 1-amlnocyclopropane-l-carboxylic acid production in apple fruits. Biologia Plantarum 29(3): 199-203.
Saudek et al., (1989) A preliminary trial of the programmable implantable medication system for insulin delivery. N Eng J Med 321(9): 574-9.

(Continued)

*Primary Examiner* — Wu-Cheng Winston Shen
*Assistant Examiner* — Christopher R Stone
(74) *Attorney, Agent, or Firm* — Rothwell, Figg, Ernst & Manbeck, P.C.

(57) ABSTRACT

The present invention relates to methods of treating benign hyperproliferative diseases of the epidermis by administering a composition comprising at least one jasmonate ester derivative. In particular, the present invention provides jasmonate ester derivatives as potent compounds useful for the treatment of disorders such as actinic keratoses with reduced side effects.

19 Claims, 9 Drawing Sheets

(56) References Cited

FOREIGN PATENT DOCUMENTS

| | | |
|---|---|---|
| JP | 06-122653 | 5/1994 |
| JP | 7-308196 | 11/1995 |
| JP | 10029935 | 2/1998 |
| JP | 11-029412 | 2/1999 |
| JP | H11-139908 | 5/1999 |
| JP | H11-140022 | 5/1999 |
| JP | 2000-333691 | 12/2000 |
| JP | 2002205921 | 7/2002 |
| JP | 2003-238331 | 8/2003 |
| WO | 02/080890 | 10/2002 |
| WO | 2004/063155 | 7/2004 |
| WO | 2005/054172 | 6/2005 |
| WO | 2006/001021 | 1/2006 |
| WO | 2007/066336 | 6/2007 |
| WO | 2007/066337 | 6/2007 |
| WO | 2008/111088 | 9/2008 |
| WO | 2008/113495 | 9/2008 |
| WO | 2010/143180 | 12/2010 |
| WO | 2011/000903 | 1/2011 |
| WO | 2011/010075 | 1/2011 |

OTHER PUBLICATIONS

Schneider et al., (1989) Separation of diastereomeric amino acid conjugates of jasmonic acid. Journal of Chromatography 483: 459-62.
Scognamiglio et al., (2012) Fragrance material review on methyl jasmonate. Food and Chemical Toxicology 50 (suppl .): S572-576.
Seto et al., (1992) Structure-Activity Relationships of (±)-Cucurbic Acid Analogs on the Root Growth of Rice Seedlings and Height of Young Corn Plants. Journal of Pesticide Science 17(1): 61-7.
Seto et al., (1999) Easy Preparation of Methyl 7-epi-Jasmonate and Four Stereoisomers of Methyl Cucurbate, and Assessment of the Stereogenic Effect of Jasmonate on Phytohormonal Activities. Biochem Biosc Biotech 63(2): 361-7.
Shafiq et al., (2013) Time of methyl jasmonate application influences the development of 'Cripps Pink' apple fruit colour. Journal of the Science of Food and Agriculture 93(3): 611-618.
Suemune et al., (1986) Conversion of Limonene to Prostanoic Acid and 8-Isoprostanoic Acid. Chemical and Pharmaceutical Bulletin 34(2): 550-7.
Suemune et al., (1987) Enzymatic Procedure for the Synthesis of 11-Deoxyprostaglandins. Chemical and Pharmaceutical Bulletin 35(5): 1741-7.
Taber and Malcolm (1998) Rhodium-Mediated Intramolecular C—H Insertion: Probing the Geometry of the Transition State. J Org Chem 63(11): 3717-21.
Ting and Morris, (1978) Reactivity of autolymphocytotoxic antibodies from dialysis patients with lymphocytes from chronic lymphocytic leukemia (CLL) patients. Transplantation 25(1): 31-3.
Tong et al., (2008) Methyl jasmonate downregulates expression of proliferating cell nuclear antigen and induces apoptosis in human neuroblastoma cells. Anti-Cancer Drugs 19(6): 573-81.
Ueda et al., (1981) Inhibitory effect of methyl jasmonate and its related compounds on kinetin-induced retardation of oat leaf senescence. Physiologia Plantarum 52(2): 305-9.
Vatela et al., (1988) Cyclic fatty acid monomers: synthesis and characterization of methyl ω-(2-alkylcyclopentyl) alkenoates and alkanoates. Chemistry and Physics of Lipids 48(1-2): 119-28.
Vippagunta et al., (2001) Crystalline solids. Adv Drug Deliv Rev 48(1): 3-26.
Wade (1991) Organic Chemistry, 2nd edition. Published by Prentice-Hall, Inc., p. 952.
Wang et al., (2005) Efficient elicitation of ginsenoside biosynthesis in cell cultures of Panax notoginseng by using self-chemically-synthesized jasmonates. Biotechnology and Bioprocess Engineering 10(2): 162-165.
Wang et al., (2007) Society for Investigative Dermatology, 86th annual meeting: abstract ID 861.

Weinges and Lernhardt (1990) Chemistry and Stereochemistry of Iridoids, XIII.—Synthesis of Enantiomerically Pure Methyl (1R,2S,2"Z)-(+)-Jasmonate Starting from Catalpol. Liebigs Annalen Der Chemie 8: 751-4 (translated abstract).
Yeruva et al., (2006) Jasmonates induce apoptosis and cell cycle arrest in non-small cell lung cancer lines. Exp Lung Res 32 (10): 499-516.
Yoneyama et al., (1998) Effect of Jasmonates and Related Compounds on Seed Germination of Orobanche minor Smith and Striga hermonthica (Del.) Benth Biosci Biotechnol Biochem 62(7): 1448-50.
Zhao et al., (2004) Novel fluoro- and hydroxyl-containing jasmonate derivatives as highly efficient elicitors in suspension cultures of Taxus chinensis. Bioorg Med Chem Lett 14(18): 4755-8.
Abu-Hamad et al., (2008) Hexokinase-I protection against apoptotic cell death is mediated via interaction with the voltage-dependent anion channel-1: mapping the site of binding. J Biol Chem 283 (19): 13482-90.
Berge et al., (1977) Pharmaceutical salts. J Pharm Sci 66: 1-19.
Bertrand et al., (2002) The BRET2/arrestin assay in stable recombinant cells: a platform to screen for compounds that interact with G protein-coupled receptors (GPCRS). J Recept Signal Transduct Res 22(1-4): 533-41.
Botham et al., (1998) Alternative methods for skin irritation testing: the current status. ECVAM Skin Irritation Task Force report 1. ATLA 26: 195-211.
Buchwald et al., (1980) Long-term, continuous intravenous heparin administration by an implantable infusion pump in ambulatory patients with recurrent venous thrombosis. Surgery 88: 507-16.
Chen et al., (2007) The Warburg effect and its cancer therapeutic implications. J Bioenerg Biomembr 39 (3): 267-74.
Cotovio et al., (2005) The in vitro skin irritation of chemicals: optimization of the EpiSkin prediction model with the framework of the ECVAM validation process. ATLA 33: 329-49.
Davies ed., Plant Hormones, Kluwer Academic Publishers, London, 2004, pp. 618, 620.
Fingrut and Flescher (2002) Plant stress hormones suppress the proliferation and induce apoptosis in human cancer cells Leukemia 16: 608-616.
Fingrut et al., (2005) Jasmonates induce nonapoptotic death in high-resistance mutant p53-expressing B-lymphoma cells. Br J Pharmacol 146(6): 800-8.
Flescher (2005) Jasmonates—a new family of anti-cancer agents. Anti-cancer Drugs 16(9): 911-6.
Flescher (2007) Jasmonates in cancer therapy. Cancer Lett 245 (1-2): 1-10.
Galluzzi et al., (2006) Mitochondria as therapeutic targets for cancer chemotherapy. Oncogene 25(34): 4812-30.
Galluzzi et al., (2008) Disruption of the hexokinase-VDAC complex for tumor therapy. Oncogene 27(34): 4633-5.
Goldin et al., (2007) Mitochondria-mediated ATP depletion by anti-cancer agents of the jasmonate family. J Bioenerg Biomembr 39(1): 51-7.
Goldin et al., (2008) Methyl jasmonate binds to and detaches mitochondria-bound hexokinase: a new mechanism of cell death. Oncogene 27 (34): 4636-43.
Gonzalez-Aguilar et al., (2001) Methyl jasmonate reduces chilling injury symptoms and enhances colour development of "Kent" mangoes. Jouranl of the Science of Food and Agriculture 81(13): 1244-1249.
Hamon et al., (1975) Synthesis of prostanoic acid. Tetrahedron Lett 16(50): 4481-2.
Heyfets and Flescher (2007) Cooperative cytotoxicity of methyl jasmonate with anti-cancer drugs and 2-deoxy-D-glucose. Cancer Lett 250(2): 300-10.
Hossain et al., (2004) Fragrances in oolong tea that enhance the response of GABAA receptors. Biochem. Biosci. & Biotech. 68(9): 1842-8.
Howes (1996) Method for assessing percutaneous absorption. The report and recommendation of ECVAM workshop 13. ATLA 24: 81-106.

(56) References Cited

OTHER PUBLICATIONS

Ishii et al., (2004) Induction of differentiation of human myeloid leukemia cells by jasmonates, plant hormones. Leukemia 18(8): 1413-9.

Jikumaru et al., (2004) Preparation and biological activity of molecular probes to identify and analyze jasmonic acid-binding proteins. Biosci Biotechnol Biochem 68(7): 1461-6.

Kang et al., (2013) Methyl 5-chloro-4,5-didehydrojasmonate (J7) inhibits macrophage-derived chemokine production via down-regulation of the signal transducers and activators of transcription 1 pathway in HaCaT human keratinocytes. Chem Pharm Bull (Tokyo) 61(10): 1002-8.

Keinan et al., (2010) Oligomerization of the mitochondrial protein voltage-dependent anion channel is coupled to the induction of apoptosis. Mol Cell Biol 30(24): 5698-709.

Kim et al., (2004) Methyl jasmonate induces apoptosis through induction of Bax/Bcl-XS and activation of caspase-3 via ROS production in A549 cells. Oncol Rep 12(6): 1233-8.

Kniazhanski et al., (2008) Methyl jasmonate induces cell death with mixed characteristics of apoptosis and necrosis in cervical cancer cells. Cancer Letters 271(1): 34-46.

Koda et al., (1991) Potato tuber-inducing activities of jasmonic acid and related compounds. Phytochemistry 30(5): 1435-8.

Kolho et al., (1993) Hepatitis C antibodies in dialysis patients and patients with leukaemia. J. Med. Virol. 40(4): 318-21.

Kondo and Fukuda (2001) Changes of jasmonates in grape berries and their possible roles in fruit development. Scientia Horticulturae 91(3,4): 275-288.

Kondo et al., (2004) Changes in Jasmonates of Mangoes during Development and Storage after Varying Harvest Times. Journal of the American Society for Horticultural Science 129(2): 152-157.

Kondo et al., (2005) Preharvest antioxidant activities of tropical fruit and the effect of low temperature storage on antioxidants and jasmonates. Postharvest Biology and Technology 36(3): 309-318.

Kramell et al CAS: 111:39842 (1988).

Kramell et al., (1988) Synthesis of n-(jasmonoyl)amino acid conjugates. Tetrahedron 44(18): 5791-807.

Kramell et al., (1997) Chiral separation of amide conjugates of jasmonic acid by liquid chromatography. Chromatographia 45(1): 104-8.

Kuzuyama et al., (1999) Cloning and expression in *Escherichia coli* of 2-hydroxypropylphosphonic acid epoxidase from the fosfomycin-producing organism, Pseudomonas syringae PB-5123. Biosci Biotechnol Biochem 63(12): 2222-4.

Lalel et al., (2003) The role of methyl jasmonate in mango ripening and biosynthesis of aroma volatile compounds. The Journal of Horticultural Science & Biotechnology 78(4): 470-484.

Mathupala et al., (2006) Hexokinase II: Cancer's double-edged sword acting as both facilitator and gatekeeper of malignancy when bound to mitochondria. Oncogene 25: 4777-86.

Michelet et al., (2012) The anti-ageing potential of a new jasmonic acid derivative (LR2412): in vitro evaluation using reconstructed epidermis Episkin™. Exp Dermatol 21(5): 398-400.

Miersch et al., (1987) Biological Activity of Jasmonic Acid Glucosyl Ester. Biochemie and Physiologie der Pflanzen 182(5): 425-428.

Mookherjee et al. (1974) International Congress of Essential Oils—CAS abstract AN1976: 405236.

Morissette et al., (2004) High-throughput crystallization: Polymorphs, Salts, Co-crystals and solvates pharmaceutical solids. Advanced Drug Delivery Reviews 56: 275-300.

Ollivier and Salaun (1985) (±)-Dicranenone A from 1-hydroxycyclopropanecarboxaldehyde derivatives. J Chem Soc Chem Commun18: 1269-70.

Palmieri et al., (2011) A preliminary study of the local treatment of preneoplastic and malignant skin lesions using methyl jasmonate. Eur Rev Med Pharmacol Sci 15(3): 333-6.

Pastorino et al., (2005) Activation of glycogen synthase kinase 3β disrupts the binding of hexokinase II to mitochondria by phosphorylating voltage-dependent anion channel and potentiates chemotherapy-induced cytotoxicity. Cancer Res 65 (22): 10545-54.

Pedersen (2007) Warburg, me and Hexokinase 2: Multiple discoveries of key molecular events underlying one of cancers' most common phenotypes, the "Warburg Effect", i.e., elevated glycolysis in the presence of oxygen. J Bioenerg Biomembr 39 (3): 211-22.

Pedersen (2008) Voltage dependent anion channels (VDACs): a brief introduction with a focus on the outer mitochondrial compartment's roles together with hexokinase-2 in the "Warburg effect" in cancer. J Bioenerg Biomembr 40 (3): 123-6.

Pedersen et al., (2002) Mitochondrial bound type II hexokinase: a key player in the growth and survival of many cancers and an ideal prospect for therapeutic intervention. Biochim Biophys Acta 1555 (1-3): 14-20.

Qian et al., (2004) Novel chemically synthesized hydroxyl-containing jasmonates as powerful inducing signals for plant secondary metabolism. Biotechnology and Bioengineering 86(7): 809-816.

Reischer et al., (2007) Effects of natural and novel synthetic jasmonates in experimental metastatic melanoma. Br J Pharmacol 150(6): 738-749.

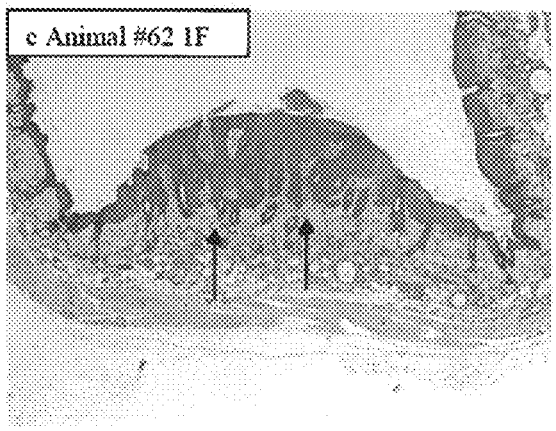 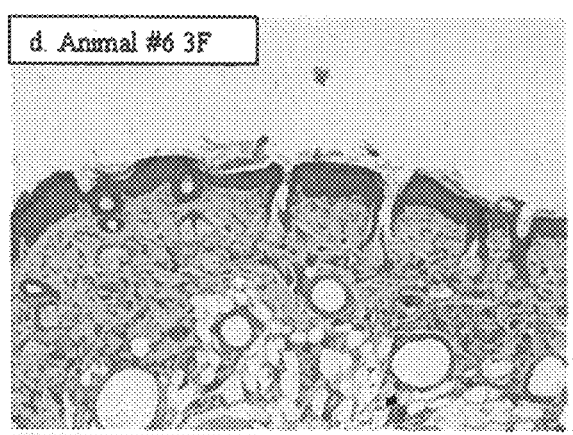
Vehicle-control
Arrows show regions of AK
2.5% Compound C
Healthy-looking skin
Figure 8A
Figure 8B

USE OF JASMONATE ESTER DERIVATIVES FOR TREATING BENIGN HYPERPROLIFERATIVE SKIN DISORDERS

CROSS REFERENCE TO RELATED APPLICATIONS

This application is a Continuation-In-Part of U.S. patent application Ser. No. 13/376,917, which is a 35 U.S.C. §371 National Phase Entry Application from PCT/IL2010/000438, filed Jun. 3, 2010, and designating the United States, which claims the benefit of U.S. Provisional Application No. 61/185,221, filed on Jun. 9, 2009, and U.S. Provisional Application No. 61/249,265, filed on Oct. 7, 2009, the contents of each of which are incorporated herein in their entireties for all purposes.

FIELD OF THE INVENTION

The present invention relates to methods of use of jasmonate ester derivatives for treating benign hyperproliferative disorders of the skin, in particular, actinic keratosis.

BACKGROUND OF THE INVENTION

Jasmonates are a family of plant stress hormones, which are released in instances of extreme UV radiation, osmotic shock, heat shock, pathogen attack and the like, to initiate various cascades. The use of jasmonates for the treatment of mammalian cancer has been disclosed in International Patent Application WO 02/080890 and in U.S. Pat. No. 6,469,061 wherein the jasmonates were shown to induce direct cytotoxicity for various types of human cancer cells derived from breast, prostate, skin, and blood cancers. Methyl jasmonate was shown to be effective in preventing development of lymphomas in mice (Fingrut and Flescher, *Leukemia,* 16: 608-616, 2002).

International Patent Application WO 2005/054172 discloses halogenated jasmonate derivatives, pharmaceutical compositions comprising the derivatives, and their use in reducing cancer cell growth and in treating cancer.

International Patent Applications WO 2007/066336 and WO 2007/066337 disclose jasmonate derivatives, pharmaceutical compositions comprising same, and use thereof in reducing cancer cell growth and the treatment of cancer.

International Patent Application WO 2008/111088 discloses an assay for identifying anti-cancer candidate drug molecules by comparing the activity of the candidate drug molecule with the activity of a jasmonate derivative known as having anti-cancer effect in at least one of the following: dissociating hexokinase from mitochondria, interfering with hexokinase binding to a voltage dependent anion channel, and binding to hexokinase directly.

Kniazhanski et al. (*Cancer Letters,* 271(1): 34-46, 2008) discloses that methyl jasmonate is cytotoxic to a range of cervical cancer cell lines. Reischer et al. (*Br J. Pharmacol.,* 150(6): 738-749, 2007) discloses that methyl jasmonate suppresses cell motility and inhibits the development of lung metastases in metastatic melanoma cells.

Wang et al. (*Society for Investigative Dermatology,* 86th annual meeting: abstract ID 861, 2007) discloses that jasmonic acid and methyl jasmonate are potential agents against UVB-induced skin cancer but have low toxicity on the malignant keratinocytes A431 cell line.

US Patent Application No. US 2003/0224024 discloses compositions of jasmonate esters, including methyl jasmonate, in the form of any cosmetic composition, including compositions for treating certain diseases of the skin, such as psoriasis. US Patent Application No. US 2010/0069497 discloses use of hydroxy jasmonate derivatives for treating psoriasis.

US Patent Application No. US 2009/0197939 discloses topical use of aromatic skin active ingredients, including methyl dihydro jasmonate for cosmetic applications, including treating skin disorders, such as seborrheic dermatitis, keratosis, psoriasis.

US Patent Application No. US 2007/0082852 relates to use of jasmonic acid for inducing proliferation of fibroblasts or keratinocytes thereby formation of new skin and gum tissues, facilitate wound healing, and ameliorate the effects of aging. It is explained that signs of aging may result from processes that include keratoses.

Skin benign hyperproliferative disorders arise from abnormal growth and differentiation of epidermal cells and may be attributed to lack of response or inappropriate response to regulating factors, or alternatively to dysfunctional regulating factors. This abnormality may develop into various benign skin disorders including, ichthyiosis, seborrhea and actinic keratoses.

Keratosis is defined as any horny growth of the skin including such growths as a wart or callous. Actinic keratosis typically is a sharply outlined verrucous or keratotic growth which may become malignant. It usually occurs in the middle aged or the elderly and is due to excessive exposure to the sun.

Actinic keratoses are potentially premalignant flat keratotic lesions considered to be either carcinoma in-situ or squamous intraepidermal neoplasia. Actinic keratoses are usually induced by ultraviolet (UV) radiation, typically from sunlight and are considered to be the most important manifestation of sun-induced skin damage. Actinic keratoses are characterized by alteration of maturation of keratinocytes from the basal layer of stratum corneum as viewed in microscopic examinations. The basal cells are enlarged, the nuclei are pleomorphic and some nuclei have nucleoli. These atypical cells replace part of or the entire thickness of epidermis (*Histology: from normal microanatomy to pathology,* Amenta et al. (Eds.), 7th Edition, PICCIN, 1997). Untreated actinic keratoses may develop into basal cell carcinoma or squamous cell carcinoma.

Traditional treatments of actinic keratoses include the use of nonsteroidal anti-inflammatory drugs (e.g. diclofenac), immune response modifiers (e.g. imiquimod), cryosurgery, photodynamic therapy, electrocautery and chemotherapy agents, all of which are accompanied by undesirable side effects.

Hence, there is an unmet need for more potent compounds useful for treating benign hyperproliferative skin disorders with reduced side effects.

SUMMARY OF THE INVENTION

The present invention is directed to methods of use of jasmonate ester derivatives for treating benign hyperproliferative skin disorders.

The present invention is based in part on the unexpected finding that jasmonate ester derivatives exhibit cytotoxic activity towards certain keratinocyte cell lines. Nowhere in the background art, is it taught or suggested that jasmonate ester derivatives as described herein may be highly effective in treating benign hyperproliferative skin disorders including actinic keratoses. Furthermore, it is now disclosed for the first time that jasmonate ester derivatives can accumulate in the basal layer of the epidermis thus leading to high concentrations of the active ingredient upon topical administration.

Surprisingly, such high concentrations in the epidermis were observed with jasmonate ester derivatives, when applied topically. Moreover, these high epidermal concentrations were shown, for the first time, to induce inhibition of proliferation of abnormal benign epidermal cells. The present invention thus provides the use of jasmonate ester derivatives as highly potent agents for treating benign hyperproliferative skin disorders with low levels of side effects.

According to one aspect, the present invention provides a method of treating a benign hyperproliferative skin disorder in a subject comprising administering to the subject an effective amount of a composition comprising at least one jasmonate ester derivative represented by the structure of formula III:

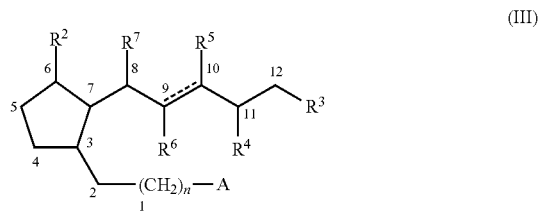

(III)

wherein
A is $COR^1$;
$R^1$ is heteroaryloxy;
$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;
$R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$,
or $R^5$ and $R^6$ together with the carbons to which they are attached form a $C_3$-$C_8$ cycloalkyl or a $C_3$-$C_8$ cycloalkyl substituted by halo;
or one of $R^5$ and $R^6$ represents an oxygen atom which is bonded to $C_6$, thereby forming an oxygen-containing 6 or 5 membered heterocyclic ring, respectively;
wherein the bond between $C_9$ and $C_{10}$ can be a single or double bond;
$R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; and
n is selected from 0, 1 and 2; including salts, hydrates, solvates, polymorphs, optical isomers, geometrical isomers, enantiomers, diastereomers, and mixtures thereof.

In one embodiment of formula III, the heteroaryloxy is unsubstituted or substituted with one or more alkyl groups. In another embodiment of formula III, $R^1$ is quinolinyloxy. In another embodiment of formula III, $R^2$ is oxo. In another embodiment of formula III, the bond between $C_9$ and $C_{10}$ is a double bond, and $R^3$, $R^4$, $R^5$, $R^6$ and $R^7$ are each hydrogen. In another embodiment of formula III, the bond between $C_9$ and $C_{10}$ is a single bond, and $R^3$, $R^4$, $R^5$, $R^6$ and $R^7$ are each hydrogen.

In one embodiment, the jasmonate ester derivative is represented by the structure of formula C:

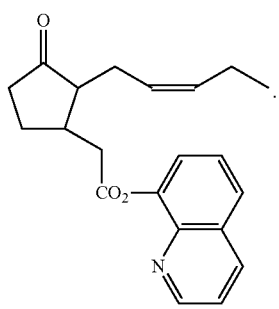

C

In some embodiments, the treatment is effectuated by exposing abnormal benign epidermal cells to a proliferation decreasing-effective amount of said compound of formula III, so as to decrease proliferation of said hyperproliferative benign epidermal cells.

According to another aspect, the present invention provides a composition comprising an effective amount of at least one jasmonate ester derivative represented by the structure of formula III for treating a benign hyperproliferative skin disorder.

In yet another aspect, the present invention provides the use of an effective amount of at least one jasmonate ester derivative represented by the structure of formula III, for the preparation of a medicament for treating a benign hyperproliferative skin disorder.

In particular embodiments, the methods disclosed herein provide the use of a composition comprising at least one jasmonate ester derivative of the present invention, formulated for topical administration.

In one embodiment, the compositions disclosed herein comprise at least one pharmaceutically acceptable excipient, carrier and/or diluent. In another embodiment, the active ingredient is dissolved in any acceptable lipid carrier. In yet another embodiment, the composition is in the form selected from an ointment, a gel and a cream. In specific embodiments, the benign hyperproliferative skin disorders to be treated according to the principles of the present invention, are selected from the group consisting of actinic psoriasis, keratoses, common warts, genital warts, keratoacanthoma, seborrhoic keratosis, seborrhea and ichthyosis. Each possibility represents a separate embodiment of the invention.

In particular embodiments, the actinic keratoses are selected from the group consisting of actinic keratosis, hypertrophic actinic keratosis, Bowenoid actinic keratosis, arsenical keratosis, hydrocarbon keratosis, thermal keratosis, radiation keratosis, chronic scar keratosis, viral keratosis, actinic cheilitis, Bowen's disease, erythroplaquia of queyrat, oral erythroplaquia, leukoplakia and intraepidermal epithelialoma. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and

BRIEF DESCRIPTION OF THE DRAWINGS

FIG. 8A: Histopathology sample from a vehicle treated animal. AK regions are indicated by arrows.

FIG. 8B: Histopathology sample from an animal treated with 2.5% Compound C. AK regions are indicated by arrows.

DETAILED DESCRIPTION OF THE INVENTION

Figure 1:
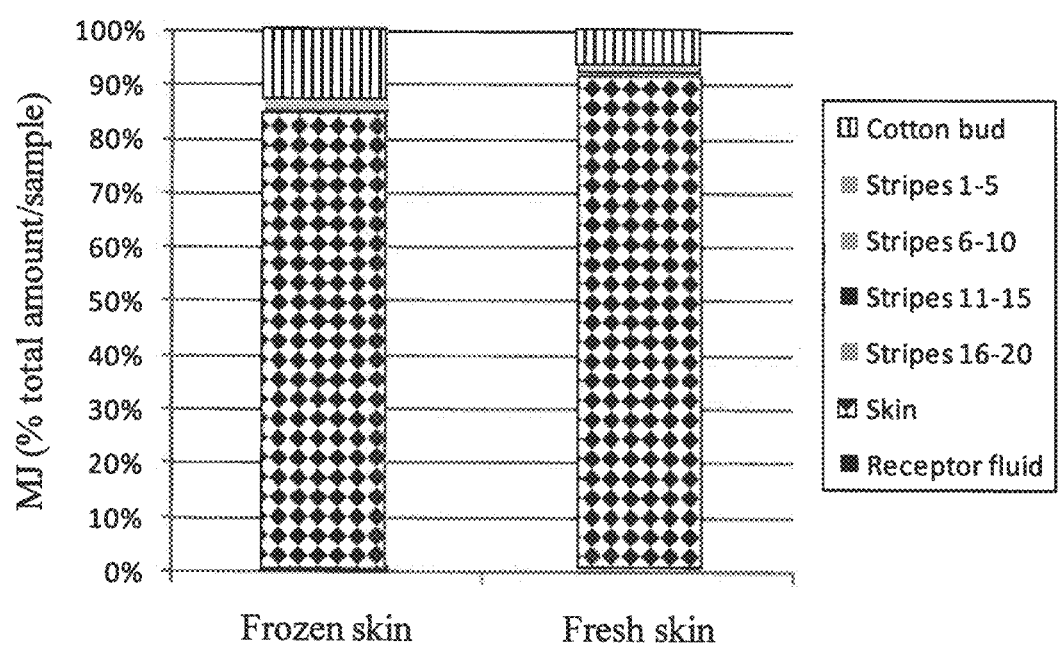
FIG. 1 shows the distribution of methyl jasmonate in skin samples.

The present invention relates to compositions comprising jasmonate ester derivatives and methods of use thereof in treating benign hyperproliferative skin disorders.

Traditional treatments of benign skin disorders such as actinic keratoses include the use of nonsteroidal anti-inflammatory drugs (e.g. diclofenac), immune response modifiers (e.g. imiquimod), cryosurgery, photodynamic therapy, and electrocautery. Alternatively, chemotherapy agents such as 5-fluorouracil, colchicine, vinblastine sulfate, cyclophosphamide, azathioprine, cyclocytidine, azacytidine, azaserine, cisplatin, cycloheximide, mechlorethamine, cycloleucine, cytarabine, decarbazine, dactinomycin, dichloromethotrexate, emetrine hydrochloride, etoposide, quanazole, hydroxyurea, idoxuridine, mercaptopurine, methotrexate, methylglyoxal bis(guanylhydrazone), metoprine, pyrimethamine, scopolamine hydrobromide, thioquanine, thiotepa, vincristine sulface, and cyclosporin A, can be used. The most common chemotherapy agent currently applied for treating benign skin disorders is 5-fluorouracil which exerts cytotoxicity to the cells by inducing inflammation of the lesion followed by cell death. However, this treatment is accompanied by harsh side effects, the most common of which include diarrhea, nausea and vomiting, mouth sores, photophobia, low blood counts and severe inflammation.

Other known treatments of benign hyperproliferative skin disorders are also accompanied by many undesirable side effects including skin irritation, scaring, inflammation, sores, crust, eczema, burning sensation, and increased sensitivity to sunlight. Thus, there is an unmet need for therapeutic modalities which exhibit potency in treating these benign hyperproliferative epidermal pathologies with reduced side effects.

The present invention provides a novel application of jasmonate ester derivatives for the treatment of benign hyperproliferative and premalignant disorders of the skin. The present invention overcomes the drawbacks of the background art by providing the use of an effective amount of a jasmonate ester derivative for treating benign hyperproliferative skin disorders without exerting substantial side effects such as irritation and corrosion of the skin.

The present invention is based on the surprising finding that jasmonate ester derivatives accumulate in the epidermis hence resulting in a substantially high level of jasmonate ester concentration, particularly in the basal layer of the epidermis. Without being bound by any theory or mechanism of action, it is contemplated that the reason for jasmonate ester accumulation is its low penetration through the epidermis. The low levels of esterases or lipases in the skin may also contribute to the accumulation of jasmonate esters in the epidermis due to its reduced conversion to jasmonic acid. Since jasmonate esters were shown to have improved stability in cutaneous penetration studies, the accumulation of jasmonate esters in the basal layer of the epidermis renders their use for treating benign hyperproliferative disorders of the skin, extremely advantageous.

Jasmonate Derivatives

Any ester derivative of jasmonate can be used in the compositions of the present invention. As used herein, the term "ester derivative" includes any natural or synthetic ester derivative of jasmonic acid including all salts, hydrates, solvates, polymorphs, optical isomers, geometrical isomers, enantiomers, and diastereomers of the particular jasmonate ester derivative; and mixtures thereof.

According to one currently preferred embodiment, the jasmonate ester derivative represented is by the structure of formula III:

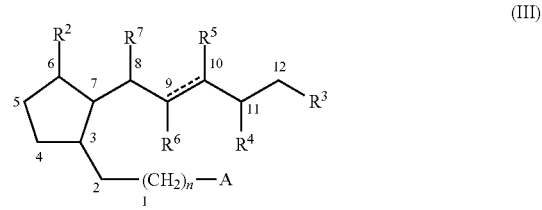

(III)

wherein
A is $COR^1$;
$R^1$ is heteroaryloxy;
$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$, or $R^5$ and $R^6$ together with the carbons to which they are attached form a $C_3$-$C_8$ cycloalkyl or a $C_3$-$C_8$ cycloalkyl substituted by halo;

or one of $R^5$ and $R^6$ represents an oxygen atom which is bonded to $C_6$, thereby forming an oxygen-containing 6 or 5 membered heterocyclic ring, respectively;

wherein the bond between $C_9$ and $C_{10}$ can be a single or double bond;

$R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; and n is selected from 0, 1 and 2; including salts, hydrates, solvates, polymorphs, optical isomers, geometrical isomers, enantiomers, diastereomers, and mixtures thereof.

In one embodiment of formula III, the jasmonate ester derivative is a compound of formula C.

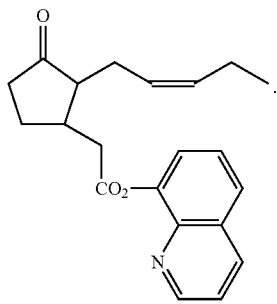

C

Other jasmonate derivatives are described hereinbelow:

In one embodiment, the jasmonate ester derivative is a compound represented by formula A:

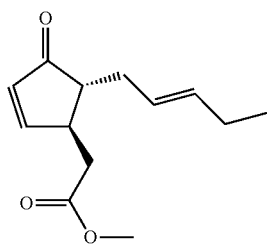

A

In another embodiment, the jasmonate ester derivative is a compound represented by formula B:

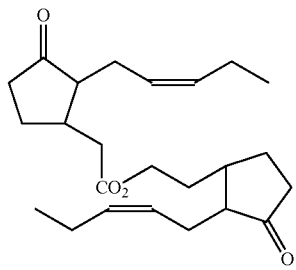

B

In other embodiments, the jasmonate ester derivative includes, but is not limited to, ester derivatives described in A) U.S. Pat. No. 6,469,061 and PCT International Patent Application Publication No. WO 02/080890; B) PCT International Patent Application Publication No. WO 2005/054172; C) PCT International Patent Application Publication No. WO2007/066336; D) PCT International Patent Application Publication No. WO2007/066337, and E) jasmonate-amino acid conjugate compounds, the contents of which are incorporated by reference herein in their entirety as if fully set forth herein. Non-limiting examples of such jasmonate derivatives include compounds represented by any of formula I through VII as set forth hereinbelow. Each possibility represents a separate embodiment of the present invention.

A) Compounds disclosed in U.S. Pat. No. 6,469,061 and WO 02/080890, represented by the structure of formula I:

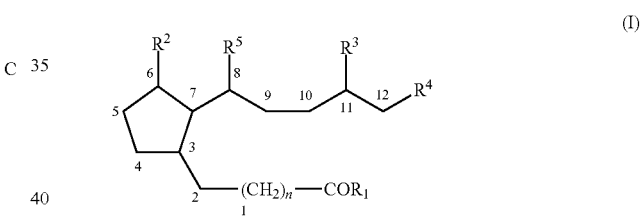

(I)

wherein:
n is 0, 1, or 2;
$R^1$ is alkoxy or O-glucosyl,
$R^2$ is OH, O, alkoxy or O-glucosyl,
$R^3$, $R^4$ and $R^5$ are H, OH, alkoxy or O-glucosyl, and/or wherein $R^1$ and $R^2$,
or $R^1$ and $R^4$ together form a lactone,
the bonds between C3:C7, C4:C5, and C9:C10 may be double or single bonds, wherein at least one of the bonds between C3:C7, C4:C5, and C9:C10 is a double bond;
and salts, hydrates, solvates, polymorphs, optical isomers, geometrical isomers, enantiomers, diastereomers, and mixtures thereof.

Exemplary jasmonate ester derivatives of formula (I) include, but are not limited to, methyl jasmonate, 6-epi-cucurbic-acid-lactone, 12-hydroxy-jasmonic-acid-lactone, methyl-dihydro-isojasmonate, tuberonic acid-O-β-glucopyranoside, cucurbic acid-O-β-glucopyranoside, and the lower alkyl esters of any of the following acids: jasmonic acid, 7-iso-jasmonic acid, 2,3-didehydrojasmonic acid, 3,4-didehydrojasmonic acid, 3,7-didehydrojasmonic acid, 4,5-didehydrojasmonic acid, 4,5-didehydro-7-iso-jasmonic acid, cucurbic acid, 6-epi-cucurbic acid, 12-hydroxy-jasmonic acid, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, 5,6-didehydrojasmonic acid, 6,7-didehydrojasmonic acid and, 7,8-didehydrojasmonic acid.

B) Compounds disclosed in WO 2005/054172, represented by the structure of formula II:

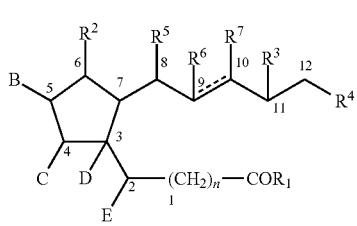

(II)

wherein n is 0, 1, or 2;

$R^1$ is $C_1$ to $C_{12}$ alkoxy, $C_1$ to $C_{12}$ substituted alkoxy, aryloxy or O-glucosyl;

$R^2$ is OH, $C_1$ to $C_{12}$ alkoxy, $C_1$ to $C_{12}$ substituted alkoxy, O-glucosyl, oxo, alkyl or imino;

$R^3$, $R^4$, $R^5$, $R^6$, $R^7$, A, B, C, D and E are each independently H, halogen, OH, $C_1$ to $C_{12}$ alkoxy, $C_1$ to $C_{12}$ substituted alkoxy, aryloxy, O-glucosyl, $C_1$ to $C_{12}$ alkyl or $C_1$ to $C_{12}$ substituted alkyl; wherein $R^1$ and $R^2$, or $R^1$ and $R^4$ may form together a lactone which is optionally substituted; wherein the bonds between C3:C7, C4:C5, and C9:C10 may independently be double bonds or single bonds;

provided that at least one of $R^3$, $R^4$, $R^5$, $R^6$, $R^7$, A, B, C, D and E is a halogen and salts, hydrates, solvates, polymorphs, optical isomers, geometrical isomers, enantiomers, diastereomers, and mixtures thereof.

Exemplary jasmonate ester derivatives of formula (II) include, but are not limited to: methyl jasmonate di-bromide (MJDB), methyl jasmonate tetrabromide (MJTB), a compound wherein $R^6$ and $R^7$ are each fluoro, a compound wherein $R^6$ and $R^7$ are each iodo, a compound wherein $R^6$ and $R^7$ are each chloro, a compound wherein one of $R^6$ and $R^7$ is iodo and the other is hydroxy, and a compound wherein one of $R^6$ and $R^7$ is iodo and the other is methoxy.

C) Compounds disclosed in WO 2007/066336, represented by the structure of formula III-A:

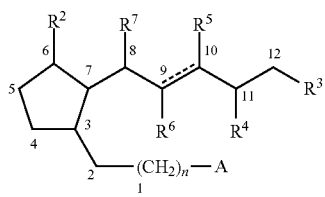

III-A wherein

A is $COR^1$;

$R^1$ is selected from the group consisting of
 a) heteroaryloxy; and
 b) —O[(CH$_2$)$_p$O)]$_m$—R$^{12}$;

$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$, or $R^5$ and $R^6$ together with the carbons to which they are attached form a $C_3$-$C_8$ cycloalkyl or a $C_3$-$C_8$ cycloalkyl substituted by halo;

or one of $R^5$ and $R^6$ represents an oxygen atom which is bonded to $C_6$, thereby forming an oxygen-containing 6 or 5 membered heterocyclic ring, respectively;

wherein the bond between $C_9$ and $C_{10}$ can be a single or double bond;

$R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

$R^{12}$ is a hydrogen or a hydroxy protecting group;

n is selected from 0, 1 and 2;

m is an integer of 1 to 20; and p is an integer of 1 to 12;

including salts, hydrates, solvates, polymorphs, optical isomers, geometrical isomers, enantiomers, diastereomers, and mixtures thereof.

Specific examples of the compounds of formula III-A include, but are not limited to:

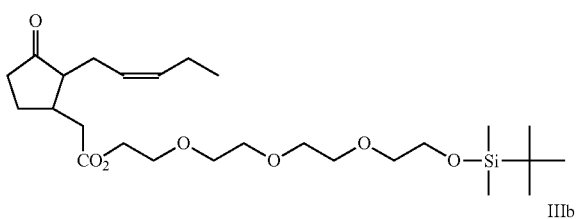

IIIa

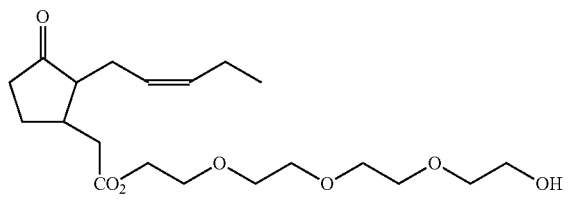

IIIb

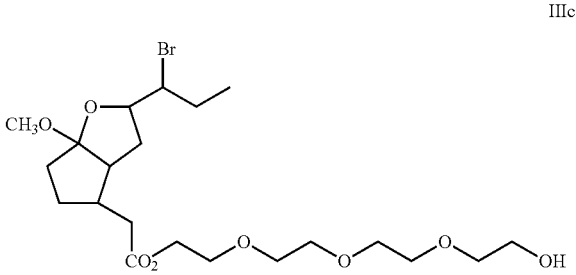

IIIc

-continued

IIId

IIIe
and

C

Another example includes a jasmonate derivative represented by the structure of formula IIIf.

IIIf

D) Compounds disclosed in WO 2007/066337, including:
  (i) Compounds represented by the structure of formula IV:

(IV)

wherein
n is 0, 1, or 2;
$R^1$ is $OR^8$;
$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, $NR^{9a}R^{9b}$, $NHCOR^{10}$ and $NHSO_2R^{11}$;

$R^3$, $R^4$, $R^5$, $R^6$ and $R^7$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can be a single or a double bond; and $R^8$, $R^{9a}$, $R^{9b}$, $R^{10}$ and $R^{11}$, are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

A non-limiting example of the compounds of formula IV is:

IVa (ii) Compounds represented by the structure of formula V:

(V)

wherein n is independently at each occurrence 0, 1, or 2;

$R^1$ is a group of the formula:

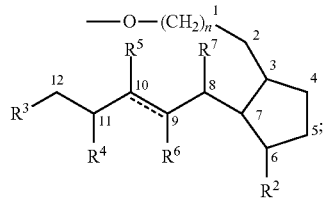

$R^2$ is independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can independently at each occurrence be a single or a double bond; and $R^8$, $R^{9a}$ and $R^{9b}$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

A specific non-limiting example of the compounds of the formula V is represented by the structure of formula Va:

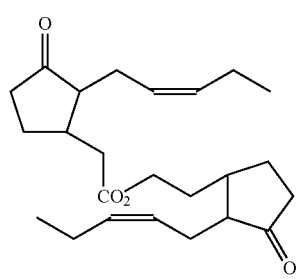

(iii) Dimeric, oligomeric or polymeric jasmonate derivatives comprising a plurality of covalently linked jasmonic acid moieties represented by the structure of formula VI:

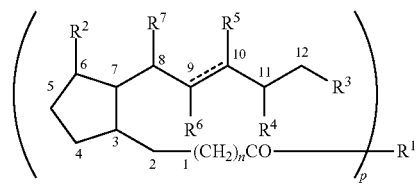

wherein n is independently at each occurrence 0, 1, or 2;

p is 2, 3, 4, 5 or 6;

$R^1$ a linker selected from the group consisting of —O—, polyoxy and a sugar moiety;

$R^2$ is independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can independently at each occurrence be a single or a double bond; and $R^8$, $R^{9a}$ and $R^{9b}$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

Specific examples of the compounds of the formula VI include, but are not limited to:

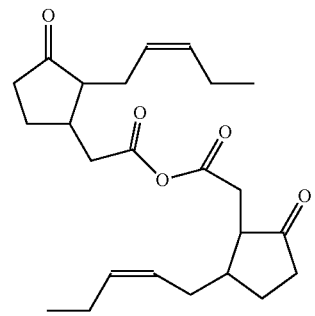

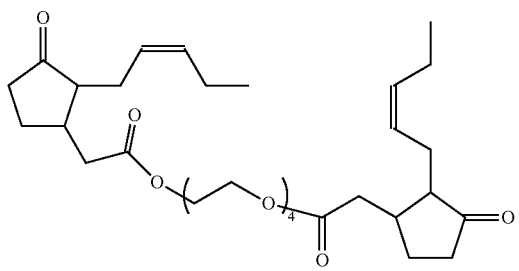

VIb e) Oligomeric compounds comprising a plurality of jasmonate moieties linked via a linker sugar moiety, represented by the structure of formula VII:

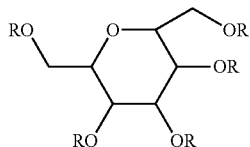

(VII)

wherein

R is represented by the formula:

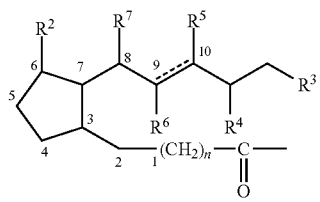

wherein each of $R^2$, $R^3$, $R^4$, $R^5$, $R^6$ and $R^7$ is as defined above.

A specific example of the compounds of the formula VII is represented by the structure of formula VIIa:

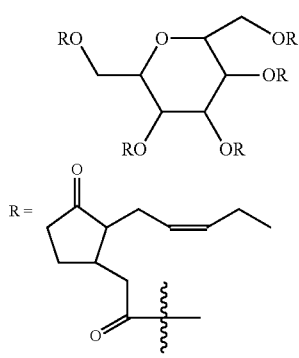

VIIa

In another embodiment, the jasmonate ester derivative is represented by the structure of formula VIII. Examples of compounds of formula VIII include compounds of formula C as described above, as well as compounds D, E and F, as described below.

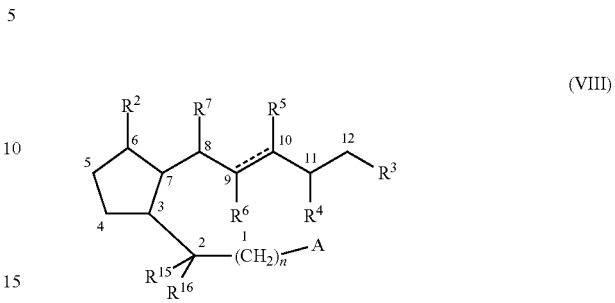

(VIII)

wherein

A is $COR^1$;

$R^1$ is heteroaryloxy;

$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$, or $R^5$ and $R^6$ together with the carbons to which they are attached form a $C_3$-$C_8$ cycloalkyl or a $C_3$-$C_8$ cycloalkyl substituted by halo;

or one of $R^5$ and $R^6$ represents an oxygen atom which is bonded to $C_6$, thereby forming an oxygen-containing 6 or 5 membered heterocyclic ring, respectively;

wherein the bond between $C_9$ and $C_{10}$ can be a single or double bond;

$R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

$R^{15}$ and $R^{16}$ are each independently selected from the group consisting of hydrogen and unsubstituted or substituted $C_1$-$C_4$ alkyl; and n is selected from 0, 1 and 2;

including salts, hydrates, solvates, polymorphs, optical isomers, geometrical isomers, enantiomers, diastereomers, and mixtures thereof.

In one embodiment, the jasmonate ester derivative is represented by the structure of formula C. In another embodiment, the jasmonate ester derivative is represented by the structure of formula D, E or F:

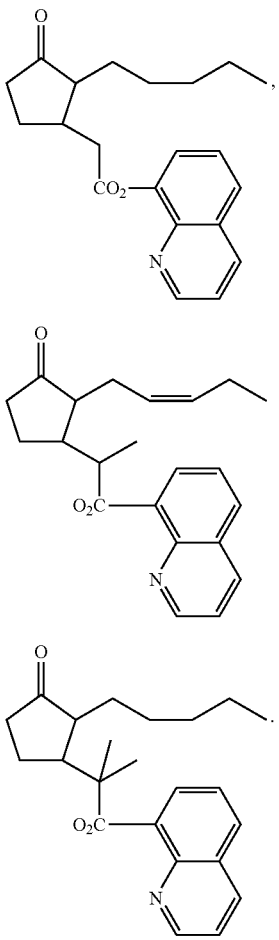

All stereoisomers of the jasmonate ester derivatives are contemplated, either in admixture or in pure or substantially pure form. The jasmonate derivatives can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R, S, D or d or L or l or d,l or D,L. In addition, several of the compounds of the invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.*, 66: 1-19, 1977. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is also contemplated.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline state of a substance, which can be characterized by particular physical properties such as X-ray diffraction, IR or Raman spectra, melting point, and the like.

Pharmaceutical Compositions

Although the compounds of the invention can be administered alone, it is contemplated that they will be administered in pharmaceutical compositions further containing at least one pharmaceutically acceptable carrier, excipient or diluent.

The pharmaceutical compositions of the present invention are formulated for topical administration, e.g. as an ointment, a gel or a cream. For topical administration to body surfaces using, for example, creams, gels, drops, ointments and the like, the compounds of the present invention can be prepared and applied in a physiologically acceptable diluent with or without a pharmaceutical carrier. Adjuvants for topical or gel base forms may include, for example, sodium carboxymethylcellulose, polyacrylates, polyoxyethylene-polyoxypropylene-block polymers, polyethylene glycol and wood wax alcohols.

Such compositions are prepared in a manner well known in the pharmaceutical art and comprise as an active ingredient at least one compound of the present invention as described hereinabove, and a pharmaceutically acceptable carrier, excipient or diluent. The term "pharmaceutically acceptable" means approved by a regulatory agency of the Federal or a state government or listed in the U.S. Pharmacopeia or other generally recognized pharmacopeia for use in mammals and, more particularly, in humans.

During the preparation of the pharmaceutical compositions according to the present invention the active ingredient is usually mixed with a carrier or excipient, which may be liquid, semi-liquid material (e.g. gel) or semi-solid material. The topical compositions of the invention can be formulated into any medium acceptable for dermatological application. For example, the compositions can be formulated into solutions, creams, lotions, emulsions, suspensions and the like.

Dermatologically acceptable excipients useful for the production of such formulations are well known to a skilled artisan and include, but are not limited to, semi-solid and liquid petroleum fractions. The petrolatum can be a synthetic or semi-synthetic hydrocarbon of the same nature as petrolatum. Mixtures of such ingredients can also be used. The preferred semi-solid material is petrolatum, commercially available from a wide variety of sources. The excipient, according to the principles of the present invention includes any synthetic or semi-synthetic oleaginous liquid fraction including, but not limited to mineral oil, and propylene glycol. Other suitable excipients include emulsifiers and thickeners selected from cetyl alcohol, stearyl alcohol, stearic acid, palmitic acid, and mixtures thereof.

Yet other suitable dermatologic ally acceptable excipients include thickeners which provide a high viscosity cream designed to local application to skin lesions. Exemplary thickeners include a mixture of a carbomer and triethanolamine. The mixture is combined together and added to the composition in an amount ranging from about 0.05 to 5 weight percent.

The formulations can additionally include lubricating agents such as talc, magnesium stearate, and mineral oil; wetting agents, surfactants, emulsifying and suspending agents; preserving agents such as methyl- and propyl-hydroxybenzoates; colorants, buffering agents (e.g., acetates, citrates or phosphates), disintegrating agents, moistening agents, antibacterial agents, chelating agents (e.g., ethylenediaminetetraacetic acid), and agents for the adjustment of tonicity such as sodium chloride.

In currently preferred embodiments, the pharmaceutical compositions of the present invention formulated for topical administration comprise one or more antioxidants. Suitable antioxidants include, but are not limited to, tocopherols (vitamin E), tocopherol derivatives, tocotrienols, ascorbic acid (vitamin C), ascorbic acid derivatives, sodium bisulfite, carotenoids, vitamin A or derivatives thereof, butylated hydroxytoluene, butylated hydroxyanisole, gallic esters, flavonoids such as, for example, quercetin or myricetin, selenium, grape seed extract, catechins such as, for example, epicatechin, epicatechingallate, epigallocatechin or epigallocatechingallate, sulfur-containing molecules such as, for example, glutathione, cysteine, lipoic acid, N-acetylcysteine, chelating agents such as, for example, ethylenediamine tetraacetic acid or other customary antioxidants. In one embodiment, antioxidants are present in a composition of the invention at about 0.1 to about 20 weight percent.

Suitable pharmaceutical carriers include, but are not limited to, sterile liquids, such as oils, including those of petroleum, animal, vegetable or synthetic origin, such as peanut oil, soybean oil, mineral oil, sesame oil and the like, polyethylene glycols, propylene glycol, glycerin, or other synthetic solvents.

The pharmaceutical compositions of the present invention may further comprise glyceryl stearate, which is a monoester of glycerine and stearic acid, or other suitable forms of glyceryl stearate (e.g. glyceryl stearate SE, which is a commercially available self-emulsifying grade of glycerol stearate that contains some sodium and/or potassium stearate). Glyceryl stearate may be in the composition anywhere from about 1 to about 3 weight percent.

According to the principles of the present invention, xanthan gum may be further added to the composition. Xanthan gum is a high molecular weight heteropolysaccharide gum produced by pure-culture fermentation of a carbohydrate with *Xanthomonas campestris*. The gum is also commercially available from various sources.

Another formulation employed in the methods of the present invention is transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

Therapeutic Use

The present invention is directed to a method of treating benign hyperproliferative skin disorders by administering to a subject a pharmaceutical composition comprising at least on jasmonate ester derivative as described herein.

Further provided in the present invention is the use of at least one jasmonate ester derivative in the preparation of a medicament for treating benign hyperproliferative skin disorders.

There is also provided in the present invention a pharmaceutical composition comprising at least one jasmonate ester derivative as described above for the treatment of benign hyperproliferative skin disorders.

The methods according to the principles of the present invention are designated for mammals, in particular, humans.

The pharmaceutical compositions comprise an effective amount of at least one jasmonate ester derivative. The term "therapeutically effective amount" or "an effective amount" as used herein refers to a quantity of a compound which is sufficient to provide a beneficial effect to the subject to which the compound is administered. The effective amount, according to the principles of the present invention can be determined by any one of ordinary skill in the art and can be tested on various models both in vitro and in vivo. A therapeutically effective amount, according to the principles of the present invention refers to an amount which improves, in a measurable manner, the differentiation of the epidermal cells as determined for example by indirect immunofluorescence analysis. Alternatively the therapeutically effective amount is an amount which can decrease, to a measurable amount, the proliferation of the cells as indicated by measurement of the activity of mitochondrial dehydrogenase enzymes of living cells (MTT assay) and by counting of basal cells level.

The term "treating" as used herein refers to alleviation of the adverse effects of the disease or disorder, which alleviation may be manifested by a decrease in at least one of the following: reduction in the number of abnormal epidermal cells (due to cell death which may be necrotic, apoptotic or any other type of cell death or combinations thereof) as compared to control; decrease in proliferation of cells, i.e. the total number of cells may increase but at a lower level or at a lower rate than the increase in control; or decrease in the invasiveness of cells (as determined for example by soft agar assay) as compared to control even if their total number has not changed.

The abnormal epidermal cells, according to the principles of the present invention, are hyperproliferative benign cells, such as human keratinocytes from psoriatic skin, and precancerous keratinocytes. The keratinocytes may be from actinic psoriasis, keratoses, keratoacanthoma, common warts, genital warts, or seborrhoic keratoses lesions. The abnormal epidermal cells may also be from other benign skin disorders such as, but not limited to, ichthyosis.

The precancerous keratinocytes, according to the principles of the present invention, are atypical epidermal keratinocytes that are characterized by at least one of the following features: nuclear pleomorphism, hyperchromatism, loss of normal cellular polarity, premature keratinization (dyskeratosis), and increased number of mitotic figures.

The term "treating benign hyperproliferative skin disorders" in the context of the present invention includes at least one of the following: a decrease in the rate of growth of the lesions; or cessation of growth of the lesions characteristic of the skin disorder. In a currently preferred embodiment, the lesions which are characteristic of the hyperproliferative skin disorder are diminished, reduced in size or totally eliminated.

The benign hyperproliferative skin disorders according to the principles of the present invention include, but are not limited to, psoriasis, actinic keratoses, common warts, genital warts, keratoacanthoma, seborrhoic keratosis, seborrhea and ichthyosis.

Actinic keratosis typically is a sharply outlined verrucous or keratotic growth which may become malignant. The term "actinic keratoses" as used in the context of the present invention includes precancerous skin lesions of keratinocytes which are areas of skin in which tissue shows the tendency to develop into cancer, although the tissue in its present state is not cancerous. Epithelial precancerous lesions include actinic keratosis (also called solar keratosis or senile keratosis), hypertrophic actinic keratosis, Bowenoid actinic keratosis, arsenical keratosis, hydrocarbon keratosis, thermal keratosis, radiation keratosis, chronic scar keratosis, viral keratosis, actinic cheilitis, Bowen's disease, erythroplaquia of queyrat, oral erythroplaquia, leukoplakia, and intraepidermal epithelialoma.

In a currently preferred embodiment, the jasmonate ester derivatives, according to the principles of the present invention, are used for the treatment of actinic keratosis. Actinic keratosis is usually present as lesions on the skin which may or may not be visually detectable exhibiting various sizes and shapes. Actinic keratosis is characterized by an inflammatory infiltration of lymphocytes, histocytes and a variable number of plasma cells. It is further characterized by the proliferation of keratinocytes.

Evaluating Therapeutic Efficiency and Determining Administration Regimen

In another embodiment, the present invention provides assays for determining the efficacy of jasmonate ester derivative in treating benign hyperproliferative skin disorders such as actinic keratoses. The assays provide a number of advantages. For instance, in various embodiments, the lack of an egg-shell, or near lack of an egg-shell allows for easier viewing and monitoring the embryo of the fertilized egg. Furthermore, in various embodiments there is greater access to the blood and allantoic waste of the fertilized egg, making it is possible to obtain blood or waste samples.

The assays of the invention are based on an animal model disclosed in WO 2006/001021, the contents of which are incorporated by reference herein in their entirety. In this model, chimeric avian embryos comprising mammalian skin grafts having a benign hyperproliferative skin serve as a convenient and efficient system for screening therapeutic treatments. Using the avian model, the various physiological and pathological processes occurring in response to treatment of the skin graft with the jasmonate ester derivatives of the invention, can be monitored. Furthermore, the assay of the invention allows examining the therapeutic effect of the tested jasmonate ester derivative on the skin graft thereby determining the therapy (administration) regimen for said jasmonate ester derivative on benign hyperproliferative skin disorder.

Although administration regimen can be determined by a skilled artisan depending on the condition and the severity of the lesions, the patient population, age, weight etc., applying the knowledge gained from the changes observed in the mammalian-avian chimeric model system, provide more accurate and powerful guidelines. The changes observed in the mammalian-avian chimeric model system upon treatment with at least one jasmonate ester derivative include, but not limited to, formation of connective tissue, inflammation and improved tissue elasticity of the skin graft. The magnitude of these changes is used to select preferred modes of administration and optimal dosage ranges. The assay may also be used to determine the therapeutic efficacy of the jasmonate ester derivative in combination with other therapeutic agent.

Thus, the compositions of the invention may be administered once-daily, twice-daily, thrice daily, once-weekly or once-monthly. In addition, the administration can be continuous, i.e., every day, or intermittently. The terms "intermittent" or "intermittently" as used herein means stopping and starting at either regular or irregular intervals. For example, intermittent administration can be administration one to six days per week or it may mean administration in cycles (e.g. daily administration for two to eight consecutive weeks, then a rest period with no administration for up to one week) or it may mean administration on alternate days.

Should the compositions of the present invention be administered as a combination therapy with additional therapeutic agents (e.g. inflammatory drugs, chemotherapy agents etc), the treatment may take place sequentially in any order, simultaneously or a combination thereof. For example, administration of a jasmonate ester derivative can take place prior to, after or at the same time as administration of the additional therapeutic agent(s). For example, a total treatment period can be decided for the jasmonate ester derivative. The additional agent(s) can be administered prior to onset of treatment with the jasmonate ester derivative or following treatment with the jasmonate ester derivative. In addition, the additional agent(s) can be administered during the period of jasmonate ester derivative administration but does not need to occur over the entire jasmonate ester derivative treatment period. In another embodiment, the treatment regimen includes pre-treatment with one agent, followed by the addition of the other agent or agents. Alternating sequences of administration are also contemplated. Alternating administration includes administration of a jasmonate ester derivative, followed by the additional agent, followed by a jasmonate ester derivative, etc.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Pharmacokinetics Studies in Human Skin

In order to test the applicability of jasmonate ester derivatives in treating benign hyperproliferative skin disorders through topical administration, samples of human skin were used to assess dermal drug delivery and percutaneous absorption of MJ. The penetration profile of MJ in human abdominal skin was analyzed using an in vitro flow-through diffusion Frantz cell, according to the OECD guidelines and ECVAM recommendations (*OECD Guideline for the testing of chemicals,* 428, Skin absorption: in vitro method, adopted Apr. 13, 2004; Hows, The report and recommendation of ECVAM workshop 13, ATLA, 24, 81, 1996). These studies were conducted by BSL-Bioservices (Planegg, Germany) and the samples were analyzed by ATC (Liege, Belgium).

Figure 2A:
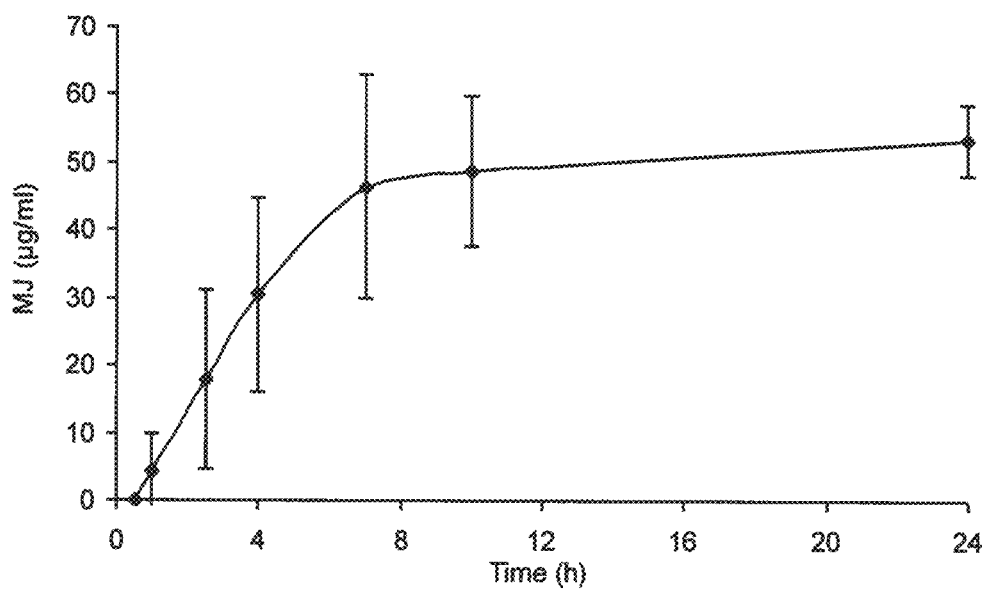
FIG. 2A presents the percutaneous absorption of methyl jasmonate in human frozen skin samples.
Figure 2B:
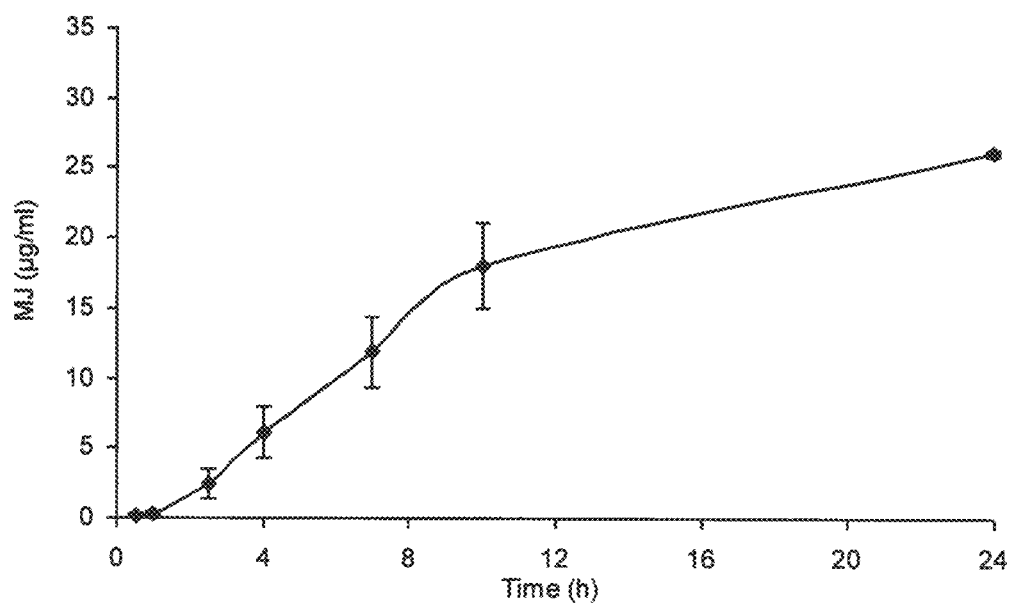
FIG. 2B presents the percutaneous absorption of methyl jasmonate in human fresh skin samples.

Two separate studies using cryo-preserved skin and fresh skin were conducted to test the percutaneous penetration of MJ. Upon application of MJ on skin patches, local intra-skin concentrations in the range of 1M were reached with no compound degradation. 24 hours after a single application, 80-90% of recovered MJ was found in the basal layer of the skin sample, corresponding mainly to epidermis and the upper part of the dermis. Approximately 0.3-1.2% was retrieved in the receptor fluid (FIG. 1). In the receptor fluid, MJ was detectable as early as one hour after application, with a plateau being reached after 8 to 12 hours characterizing a rapid skin penetration of the compound (FIGS. 2a and b).

Thus, it is clearly shown that MJ is easily absorbed in the skin and accumulates in the epidermis. These permeation studies on human skin indicate that compound degradation does not occur upon topical application of MJ thus enabling retention of very high concentration of MJ in the epidermis within the range of 1 mole/L.

Example 2

Toxicity of Jasmonate Ester Derivatives in Human Skin—Skin Irritation Assay

Acute irritation is a local, reversible inflammatory response of normal living skin to direct injury caused by the application of an irritant substance.

In order to test the toxicity of jasmonate ester derivatives in human skin, skin irritation assay using a reconstituted three-dimensional human epidermis model (EPISKIN-Standard Model™; conducted at BSL-Bioservices, Planegg, Germany) was performed. This skin model uses normal (non-cancerous), adult human-derived epidermal keratinocytes which have been cultured to form a multilayered, highly differentiated model of human epidermis with a functional stratum corneum.

In particular, MJ was applied topically to the EPISKIN-SM™ tissue for 15 minutes followed by a 42 hours post-incubation period and immediate determination of cytotoxic effects via MTT reduction assay. Irritant potential of the compound was assessed from the relative mean tissue viabilities obtained compared to the corresponding negative control tissues concurrently treated with Aqua Dest (distilled water). The release of Interleukin-1α (IL-1α) into the tissue culture medium was determined to confirm the obtained results.

MJ showed no irritant effects providing a mean relative viability >50% and IL-1α release ≤60 pg/ml (Table 1). MJ is thus classified as "non-irritant" according to the ECVAM SIVS recommendations.

TABLE 1

Skin irritation assay

| | Negative control Aqua Dest | MJ | Positive control 5% SDS solution |
|---|---|---|---|
| Mean relative tissue viability (%) (MTT reduction) | 100 ± 6.7 | 106.7 ± 5.3 | 3.3 ± 0.6 |
| IL-1α release (pg/ml) | 12.2 ± 7.9 | 28.3 ± 6.9 | 236.7 ± 23.0 |

Example 3

Toxicity of Jasmonate Ester Derivatives in Human Skin—Skin Corrosion Assay

Skin corrosion refers to the production of irreversible tissue damage in the skin following the application of a test material.

In order to test the toxicity of jasmonate ester derivatives in human skin, skin corrosion assay using a reconstituted three-dimensional human epidermis model (EpiDerm™ skin model from MatTek, conducted at BSL-Bioservices, Planegg, Germany) was performed. This skin model uses normal (non-cancerous), human-derived epidermal keratinocytes which have been cultured to form a multilayered, highly differentiated model of human epidermis with functional skin layers (basal, spinous, granular and cornified) analogous to those found in vivo.

In particular, MJ was applied topically to the EpiDerm™ tissue and incubated for 3 and 60 minutes at each time. After the incubation period, tissue viability was assessed via MTT reduction assay. The corrosive potential of MJ was assessed from the relative mean tissue viabilities obtained after 3 and 60 minutes compared to the corresponding negative control tissues concurrently treated with Aqua Dest (distilled water).

Using the EpiDerm™ skin model no corrosive effects were seen providing a mean relative tissue viability ≥50% after 3 min treatment and ≥15% after 60 min treatment (Table 2). MJ is thus classified as "non-corrosive" according to the OECD Guideline and the EC Commission Regulation.

TABLE 2

Skin corrosion assay

| | Negative control Aqua Dest | MJ | Positive control 8N KOH |
|---|---|---|---|
| Mean relative tissue viability (%) (MTT reduction) after 3 minutes | 100 ± 10.6 | 106 ± 2.4 | 26 ± 5.3 |
| Mean relative tissue viability (%) (MTT reduction) after 60 minutes | 100 ± 2.4 | 94 ± 2.7 | 14 ± 3.7 |

Example 4

Populations Recruited for Clinical Studies of Actinic Keratosis

Inclusion Criteria:
1. Male or Female at least 18 years of age having one actinic keratosis lesion on the shoulders, chest, back or arms.
2. The longest diameter of the selected lesion is between 3 mm and 15 mm.
3. Screening laboratory values within the references ranges (as defined by the laboratory) or alternatively the values are "out of range" with acceptable variations.
4. Ability to follow study instructions, to complete all study requirements and having signed a written consent including a consent for photographs of the selected lesion to be taken and used as part of the study data package.

Exclusion Criteria:
1. Females of child bearing potential.
2. Hypertrophic actinic keratoses.
3. Wherein the location of the selected actinic keratoses is:
   (i) within 5 cm of a scar.
   (ii) within 5 cm of any actinic keratosis lesion which is not selected for treatment.
   (iii) within 5 cm of an incompletely healed wound.
   (iv) on the breast.
   (v) within 5 cm of an area previously treated with surgical excision.
4. Presence of suspected basal cell carcinoma or squamous cell carcinoma within 5 cm of the selected treatment area.
5. Presence of known or suspected metastatic disease.
6. History or evidence of skin conditions other than actinic keratosis which would interfere with the evaluation of the study medication (e.g. eczema, unstable psoriasis, xeroderma pigmentosa).
7. A cosmetic or therapeutic procedure (e.g. liquid nitrogen, curettage, dermabrasion, medium or deep chemical peeling, laser resurfacing) located within 10 cm of the actinic keratosis lesion selected for treatment in the three months preceding the study, or anticipated treatment within 10 cm of the selected lesion during the study.
8. A cosmetic or therapeutic procedure located anywhere on the body in the four weeks preceding the study.
9. Treatment with 5-fluorouracil, imiquimod, diclofenac, masoprocol, or photodynamic therapy for lesions located within 10 cm of the actinic keratosis lesion selected for treatment in the three preceding the study.
10. Treatment with 5-fluorouracil, imiquimod, masoprocol, or photodynamic therapy for lesion located anywhere on the body in the four weeks preceding the study.
11. Previous treatment with other immunomodulators (e.g. vinblastine, podophyllin, colhamin, camptothecin), cytotoxic drugs (e.g. cyclophosphamide, azathioprine, chlorambucil, nitrogen mustard, methotrexate), or interferon/interferon inducers (other than imiquimod) in the four weeks preceding the study.
12. Previous treatment with psoralen plus UVA or use of UVB therapy on the six months preceding the study.
13. Patients who are excessively exposed to ultraviolet light (e.g. sunlight, tanning beds) during the study.
14. Use of medications that suppress the immune system (e.g. cyclosporine, prednisone, methotrexate, alefacept, infliximab) in the four weeks preceding the study.
15. Use of topical retinoids or light chemical peeling located within 10 cm of the actinic keratosis lesion selected for treatment in the four weeks preceding the study.
16. Use of systemic retinoids (e.g. isotretinoin, acitretin, bexarotene) in the six months preceding the study.
17. Use of acid containing products (e.g. salicylic acids or fruit acids such as α- and β-hydroxy acids and glycolic acids) located within 10 cm of the actinic keratosis lesion selected for treatment in the four weeks preceding the study.
18. Anticipated need to use acid containing products (e.g. salicylic acids or fruit acids, such as α- and β-hydroxy acids and glycolic acids) on the treatment area during the study.
19. Concurrent disease that suppresses the immune system (e.g. HIV).
20. Uncontrolled systemic disease (e.g. uncontrolled hypertension).
21. Anticipated need for surgery or hospitalization during the study.
22. Current evidence of chronic alcohol or drug abuse.
23. Current enrollment in an investigational drug or device study or participation in such a study in the 30 days preceding the study.

Example 5

Efficacy of Jasmonate Ester Derivatives in Treating Actinic Keratosis

In order to test the efficacy of jasmonate ester derivatives in treating actinic keratosis, 20 adult individuals having four or more clinically diagnosed actinic keratosis lesions of an approximate size of 25 $cm^2$ on sun exposed areas, in the shoulders, chest, back or arms are tested with a pure solution of methyl jasmonate. A total of 10 individuals are administered with a placebo as control population. Individuals who are excluded from the study are those who received any of the following treatments in the 30 days preceding the study: psoralen plus UVA therapy; UVB therapy; laser abrasion; dermabrasion or chemical peel. Throughout the study and in the 4 weeks preceding it, the following treatments are not allowed: topical retinoids, 5-fluorouracil, cryodestruction, chemodestruction, surgical excision, photodynamic therapy, curettage, interferon/interferon inducers, cytotoxic drugs, drugs with major organ toxicity, immunomodulators, immunosuppressive therapies, oral corticosteroids, or topical steroids anywhere on the treatment areas.

Treatment is performed by a daily administration of MJ or Placebo for 16 consecutive weeks, followed by a post-study period of 8 weeks. Approximately 10 μl of MJ or Placebo is applied topically over the lesion area.

The monitoring is performed as follows:
1. Initiation of administration (t=0): blood sampling is performed for the determination of pharmacokinetic parameters after the administration of the first dose.
2. t=3 days: haematological and biochemical assessments are performed for the evaluation of treatment tolerance.
3. t=4 weeks.
4. t=8 weeks.
5. t=16 weeks: end of treatment.
6. t=24 weeks: end of study.

Patients who discontinue the treatment period are asked to return for an assessment 8 weeks after their last dose treatment.

Efficacy, adverse events evaluation and photography are performed on each visit. Efficacy is evaluated by clinical counting and recording of the number of actinic keratosis present in the lesion area. The primary efficacy variable is the complete clearance rate, defined as the proportion of participants that have a total count of 0 clinically visible actinic keratosis lesions in the area that has been treated for a total of 8 weeks. The secondary efficacy variable is the partial clearance rate, defined as the proportion of participants that have at least a 75% reduction in the number of actinic keratosis lesions in the area that has been treated for a total of 8 weeks, in comparison to the initial number of actinic keratosis lesions.

Phase II double blind placebo study is then performed in order to assess the safety and efficacy of MJ in treating actinic keratosis. Safety of MJ in actinic keratosis patients is assessed for the administration of 10 μl pure solution of MJ applied topically over a 25 $cm^2$ treatment area surrounding a target lesion. The administration regimen is once daily for 16 consecutive weeks. Efficacy is assessed at 4 weeks, 8 weeks, 16 weeks and additional 8-weeks post-treatment.

Example 6

Tolerated Regimen and Safety of Jasmonate Ester Derivatives in Treating Actinic Keratosis In order to test the tolerated regimen and safety of jasmonate ester derivatives in treating actinic keratosis, MJ is administered (10 µl gel applied topically over a 25 cm² treatment area surrounding a target lesion) once daily (hereinafter regimen A) or alternatively on odd days for 57 consecutive days (hereinafter regimen B) to patients with actinic keratosis (AK). Three patients are entered initially at each regimen to prevent the a regime limiting toxicity which is defined as 'severe' local skin reactions which appear either prior to treatment on even days (following treatment on Day 1) or observed on Day 8 (following the end of the treatment). If no RLT and/or systemic toxicity are observed, the patients who have not been treated are split into two groups; each group is subjected to a different administration regimen (A or B). Systemic absorption and local tolerability are assessed on Day 1 and Day 8. The clinical efficacy of MJ at both regimes for 8 consecutive weeks is assessed through measurements of hematologic and biochemical parameters along with cosmetic assessment that are undertaken at the screening visit on Day 0, Days 8 and Day 57. Adverse events are assessed at every study visit. Clinical response to treatment is assessed on Days 8 and Day 57 and additionally 8 weeks after the last dose treatment.

Phase II study is then performed in order to assess optimal regimen of MJ in treating actinic keratosis. Optimal tolerated regime of MJ in actinic keratosis patients is assessed when administered once daily or alternatively only on odd days for 56 consecutive days of 10 µl pure solution of MJ applied topically over a 25 cm² treatment area surrounding a target lesion. Efficacy is assessed at 8 and 57 days after application of MJ at the optimal tolerated regime in the expanded cohort.

Example 7

Avian Model of Benign Hyperproliferative Skin Disorders

In order to test the effect of jasmonate ester derivatives on benign hyperproliferative disorders of the skin, intact mammalian skin explants grafted on the chorioallantoic membrane (CAM) of a fertilized avian are used as an animal model for actinic keratoses or psoriasis. This model is disclosed in PCT international application publication number WO 2006/001021, the contents of which are incorporated by reference herein in their entirety as if fully set forth herein.

Briefly, freshly-laid fertile chicken eggs are stored at 15° C. until required. The eggs are then warmed for one hour to room temperature, followed by vertical (with the point down) incubation in a humid atmosphere at 37° C. for 5-10 days before use. On the third day of incubation, the eggs are turned upside down, and a small hole is made in the sharp side of the egg after cleaning with a tissue impregnated with 70% ethanol. This creates an artificial air sac so that the CAM can be accessed later on without causing bleeding.

Human actinic keratosis or psoriatic lesions are removed from patients. The skin is pinned out in a petri dish with a rubber bottom, and cut into rectangular/square pieces approximately 5-10 mm on each side using scissors, scalpels or dermatological punches. The skin is stored at 15° C. in PBS$^{++}$ until grafting. Approximately 3-6 mm diameter punch biopsies of full thickness human skin are cultured at an air-liquid interface on a plastic mesh insert in 12-well culture plates in MEM medium (high Ca$^{++}$, 10% fetal calf serum and antibiotics.

Eggs with an artificial air sac are opened with iris scissors in a sterile hood. The ectodermal surface of the CAM is abraded by touching it briefly with a sterile piece of lens tissue to improve the adherence of the graft. Each piece of skin is then gently placed on the CAM and stretched out. The eggs are then sealed with adhesive tape, and returned to the incubator.

After grafting of the punch biopsies of human actinic keratosis or psoriatic lesions, the lesions are allowed to incubate for 2 days in order to allow for the skin to incorporate, and then the adhesive tape sealing of the samples is reopened. Methyl jasmonate is topically applied to different skin samples at different concentrations using a small plastic ring cut from a pipette tip. The samples are then resealed and returned to the incubator for an addition three days, whereupon they undergo routine histological and immunochemical analysis using Abs for the proliferation marker PCNA. PCNA$^+$ cells are counted in several sections, and the length of the epidermis in the section measured. Analysis includes skin fixation in 4% paraformaldehyde or Bouin's fluid, followed by paraffin embedding, cutting into 6 µm sections and staining either with hematoxylin and eosin (H&E) or immunostaining with skin specific keratin antibodies (K10, K14), and counterstaining with Hoechst nuclear staining.

Example 8

Efficacy of Compound C in an Actinic Keratosis Cell Line

Figure 3:
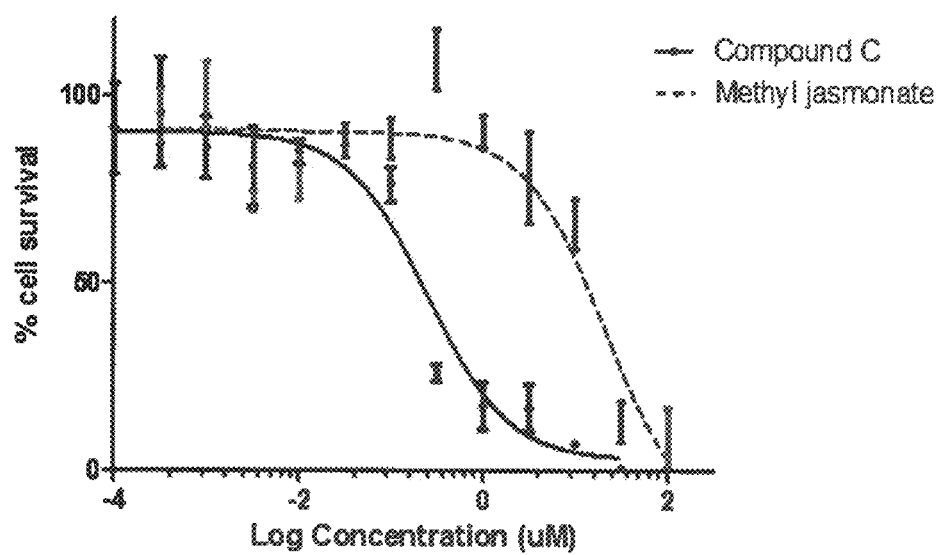
FIG. 3 shows the percent cell survival in an actinic keratosis cell line HT297.T. after treatment with Compound C or methyl jasmonate.

The effects of Compound C vs. methyl jasmonate on cell survival were evaluated in an actinic keratosis (AK) cell line HT297.T. Cells were treated with Compound C, a representative jasmonate ester derivative covered by Formula III, or methyl jasmonate at various concentrations for 3 days, followed by performing a proliferation assay using XTT (sodium 2,3,-bis(2-methoxy-4-nitro-5-sulfophenyl)-5-[(phenylamino)-carbonyl]-2H-tetrazolium inner salt) reagent. IC50 values were calculated from the mean of triplicate wells for each experiment. As shown in FIG. 3, Compound C was unexpectedly a much more potent inhibitor of cell growth as compared with methyl jasmonate in this assay. The IC50s are quantified in Table 3:

TABLE 3

|  | Compound C | Methyl jasmonate |
|---|---|---|
| IC50 (uM) | 0.25 | 21.1 |

Example 9

Efficacy of Compound C on Skin Lesion Formation Induced by UVB: A Damaged Skin Mouse Model The efficacy of Compound C was further evaluated in an animal model of Actinic Keratosis (AK). The purpose of the study was to determine the effect of compound C against lesion formation in UVB-damaged skin in SKH-1 mice, a mouse model of AK and non-melanoma skin cancers.

The study was divided to two parts: pre-study that included UVB irradiation to induce the damage to the skin, and efficacy study that included the treatment with Compound C compared to standard treatment and efficacy evaluation. After 16 weeks of UVB irradiation, 60% of the animals developed lesions, and treatment was started on week 17 and continued for 7.5 weeks. The total duration of the study was 23.5 weeks.

Group Allocation:

The study included female mice, 6-8 weeks of age at study initiation. After 16 weeks of UVB irradiation, when 60% (36/60) of the animals developed at least 1 lesion, mice were randomly stratified into 12 mice per group (see Table 4) according to score and number of lesions. Picato gel (Ingenol mebutate, Leo Pharma Inc.) was used as the positive control. At the beginning of week 17, animals were treated as set forth in Table 4.

TABLE 4

Group Allocation

| Group No. | Animal No. | Topical Treatment | Dose | Volume (μl) | Regimen |
|---|---|---|---|---|---|
| 1F | 12 | Vehicle | 1% | 50 | Daily 5 times a week |
| 2F | 12 | Positive Control (Picato) | 0.05% | 50 | Two consecutive days |
| 3F | 12 | Cpd C | 2.5% | 50 | Daily 5 times a week |
| 4F | 12 | Cpd C | 5% | 50 | Daily 5 times a week |
| 5F | 12 | Cpd C | 40% | 50 | Daily 5 times a week followed by two weeks off (a 3 week cycle; total of 3 cycles) |

For UVB irradiation, Vilber-Lourmat (France) Lamp VL-6.M was used, irradiating at 312 nm with an intensity of 0.89 mW/cm$^2$ at a distance of 15 cm. Determination of UVB irradiation Minimal Erythemal Dose (MED) was performed prior to the beginning of the study (during the pre-study period). Animals were UVB irradiated during different time periods (starting at 30 sec) and the presence of erythema was recorded 24 and 48 hours later.

Clinical Scoring of Erythema and Edema

Observations for clinical scoring and signs of erythema and edema, were performed twice a week. Erythema and edema scoring were performed according to the grading levels described in Table 5 below. Lesion numbers were determined once a week during Weeks 4-6 and twice a week during Weeks 7-16 until treatment started. During treatment, lesion number and erythema-edema scores were performed twice a week. The Erythema and Edema scoring scale is presented in Table 5:

TABLE 5

Erythema and Edema Scoring

| | Numerical Grading |
|---|---|
| Erythema and Eschar Formation | |
| No erythema | 0 |
| Very slight erythema (barely perceptible) | 1 |
| Well-defined erythema | 2 |
| Moderate erythema | 3 |
| Severe erythema (beet redness) to eschar formation preventing grading of erythema | 4 |

TABLE 5-continued

Erythema and Edema Scoring

| | Numerical Grading |
|---|---|
| Edema Formation | |
| No edema | 0 |
| Very slight edema (barely perceptible) | 1 |
| Well-defined edema (edges of area well-defined by definite raising) | 2 |
| Moderate edema (raised approximately 1 mm) | 3 |
| Severe edema (raised more than 1 mm and extending beyond exposure area) | 4 |

Results

Figure 4:
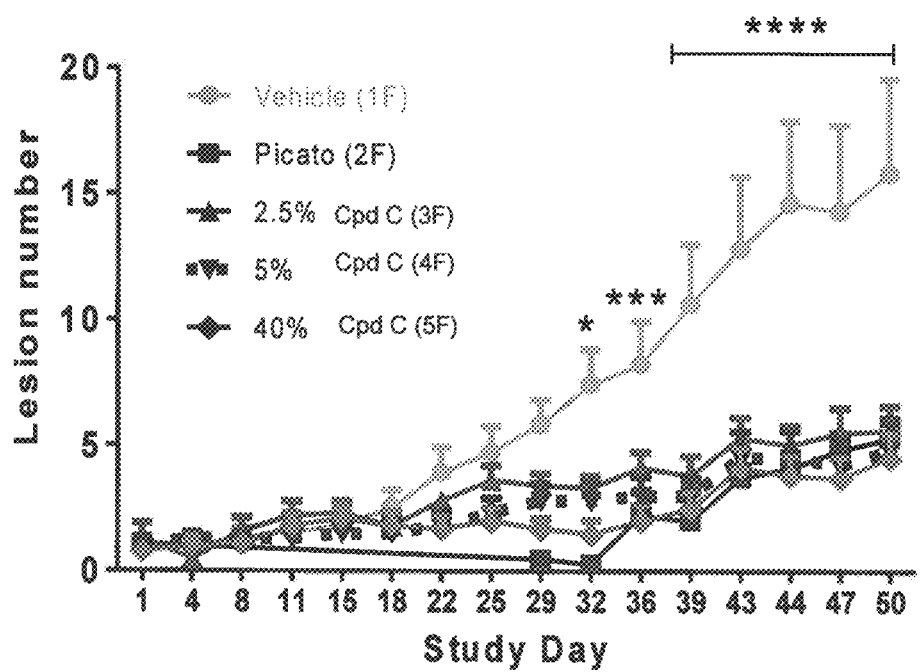
FIG. 4 shows average lesion number per treatment area after treatment with Compound C, in UVB-damaged skin of SKH-1 hairless mice. Statistics shown comparing group 1F (vehicle) to 5F (40% Compound C). * $p<0.05$; * $p<0.001$; ** $p<0.0001$ compared to the vehicle treated group (1F), using Two-way ANOVA followed by Bonferroni's multiple comparisons post-hoc test.

1. Lesion Number During the Treatment Period:

As shown in FIG. 4, lesion formation was significantly attenuated in all the treated groups compared to the vehicle treated group (1F). Statistical significance of the difference was increased with time, for example for group 5F treated by 40% Compound C p<0.05 on Day 32, p<0.001 on Day 36, and p<0.0001 on Day 39 through Day 50. These indicate a dose response of the efficacy onset. The evaluation of the lesion number in group 2F treated with Picato was not possible during days 4-29 due to scar formation on the skin that interfered with the lesion score.

Thus, Compound C led to a significant reduction in the number of lesions (p<0.0001), which is comparable with the positive control Picato.

2. Total Lesion Area

Figure 5A:
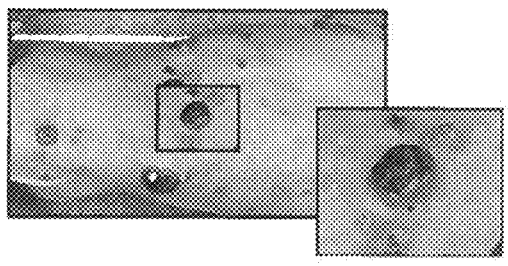
FIG. 5A shows representative pictures of UVB-induced skin lesions in SKH-1 hairless mice after treatment with vehicle. Treatment began after lesions began to form.
Figure 5B:
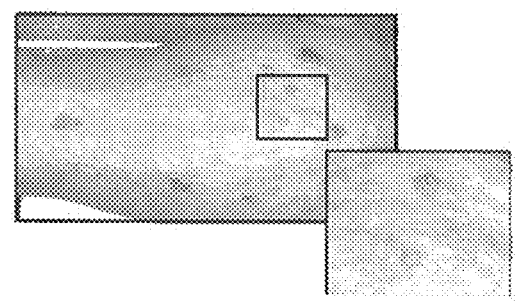
FIG. 5B shows representative pictures of UVB-induced skin lesions in SKH-1 hairless mice after treatment of 5% compound C. Treatment began after lesions began to form.
Figure 6:
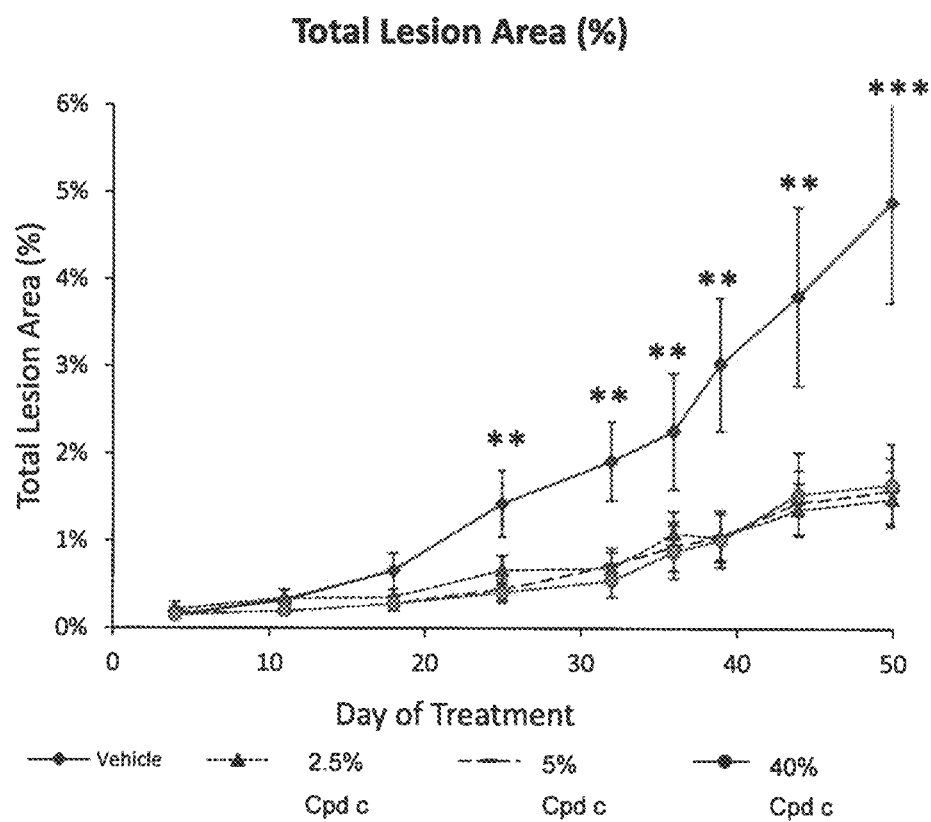
FIG. 6 shows the total lesion area (%) after treatment with Compound C at the indicated concentrations, in UVB-damaged skin of SKH-1 hairless mice. $p<0.01$; * $p<0.001$ using two-way ANOVA followed by Bonferroni's post-hoc test comparisons.
Figure 7:
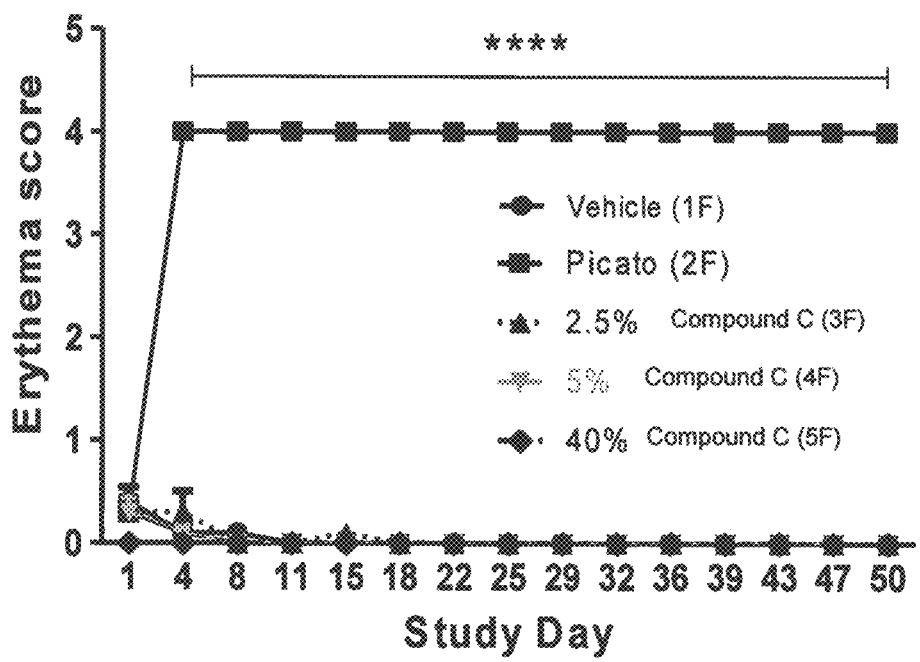
FIG. 7: Group average of erythema scores during the treatment period, after treatment with vehicle (1F), Picato (2F), or the indicated concentrations of Compound C. $p<0.0001$ compared to the vehicle treated group (1F) when using two-way ANOVA followed by Bonferroni's multiple comparisons post-hoc test.

Compound C also led to a 70% reduction in total area of lesions and total tumor area as exemplified in FIGS. 5 and 6. In FIG. 6, p<0.01; * p<0.001 using two-way ANOVA followed by Bonferroni's post-hoc test comparisons 3. Erythema and Edema Scoring During Treatment Period Significant signs of erythema were observed only in group 2F treated by Picato (FIG. 7). Erythema (eschar formation) in group 2F started on Day 4 after Picato application and lasted during all the study period. Slight erythema was observed in group 3F on Day 4 only and disappeared by Day 8. In group 5F, no erythema was observed on Day 1 and thereafter.

Throughout the pre-study and study, edema was not observed in all treated groups except in group 2F after the application of Picato and before the eschar formation on Day 4.

4. Histopathology

Histopathology evaluation confirms that the groups treated with compound C look similar to naïve (healthy) animals. Thus, not only does compound C display a clinical effect in terms of the total lesion number/area, but an effect is also seen at the tissue level as seen in histopathology analysis. FIG. 8A shows a sample from a vehicle treated animal (control). AK regions are indicated by arrows. FIG. 8B shows a slide from an animal treated with 2.5% compound C, demonstrating healthy looking skin as a result of treatment.

CONCLUSIONS

In conclusion, all the animals treated with Compound C, at all doses (2.5% (3F), 5% (4F) and 40% (5F)), showed no skin erythema or edema following topical treatment. Picato (0.05%) treatment (2F) was associated with severe skin reaction (both erythema and edema) and scarring that was followed by formation of large tumors on the scarred area.

Lesion formation was significantly attenuated in all the treated groups compared to the Vehicle treated group (1F). There seemed to be some dose related response in the appearance of statistically significant onset. The maximal reduction in lesion number on Day 50 was similar in all treated groups: 66% for Picato (2F), 65% for Compound C 2.5% (3F), 70% for Compound C (4F) and 72% for Compound C 40% (5F).

No abnormality was detected in gross pathology examination performed on animals from group 5F treated with 40% VDA1102.

Thus, it is hereby demonstrated that Compound C has beneficial effects on skin lesion formation induced by UVB: a damaged skin mouse model of Actinic Keratosis.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method of treating a benign hyperproliferative skin disorder in a subject in need thereof, comprising the step of decreasing proliferation of abnormal hyperproliferative benign epidermal cells in said subject by exposing said cells to a proliferation decreasing-effective amount of a pharmaceutical composition comprising at least one jasmonate ester of formula III, so as to decrease proliferation of said hyperproliferative benign epidermal cells:

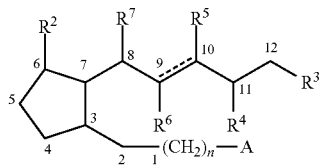

(III)

wherein
A is $COR^1$;
$R^1$ is quinolinyloxy;
$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;
$R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$,
or $R^5$ and $R^6$ together with the carbons to which they are attached form a $C_3$-$C_8$ cycloalkyl or a $C_3$-$C_8$ cycloalkyl substituted by halo;
or one of $R^5$ and $R^6$ represents an oxygen atom which is bonded to $C_6$, thereby forming an oxygen-containing 6 or 5 membered heterocyclic ring, respectively;
wherein the bond between $C_9$ and $C_{10}$ can be a single or double bond;
$R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; and n is selected from 0, 1 and 2;

including salts, hydrates, solvates, polymorphs, optical isomers, geometrical isomers, enantiomers, diastereomers, and mixtures thereof.

2. The method according to claim 1, wherein the quinolinyloxy is unsubstituted or substituted with one or more alkyl groups.

3. The method according to claim 1, wherein $R^2$ is oxo.

4. The method according to claim 1, wherein the bond between $C_9$ and $C_{10}$ is a double bond, and $R^3$, $R^4$, $R^5$, $R^6$ and $R^7$ are each hydrogen.

5. The method according to claim 1, wherein the bond between $C_9$ and $C_{10}$ is a single bond, and $R^3$, $R^4$, $R^5$, $R^6$ and $R^7$ are each hydrogen.

6. The method according to claim 1, wherein the jasmonate ester is represented by the structure of formula C:

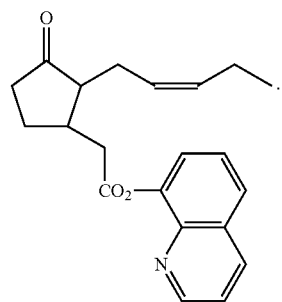

7. The method according to claim 1, wherein the composition is formulated for topical administration.

8. The method according to claim 7, wherein the composition is in a form selected from the group consisting of an ointment, a cream a lotion, a foam and a gel.

9. The method according to claim 1, wherein the benign hyperproliferative skin disorder is selected from the group consisting of psoriasis, keratoses, actinic keratosis, common warts, genital warts, keratoacanthoma, seborrhoic keratosis, seborrhea and ichthyosis.

10. The method according to claim 9, wherein the keratoses are selected from the group consisting of actinic keratosis, hypertrophic actinic keratosis, Bowenoid actinic keratosis, arsenical keratosis, hydrocarbon keratosis, thermal keratosis, radiation keratosis, chronic scar keratosis, viral keratosis, actinic cheilitis, Bowen's disease, erythroplaquia of queyrat, oral erythroplaquia, leukoplakia or intraepidermal epithelialoma.

11. The method according to claim 9, wherein the skin disorder is actinic keratosis.

12. A method of treating actinic keratosis in a subject in need thereof, comprising the step of decreasing proliferation of abnormal hyperproliferative epidermal cells in said subject by exposing said cells to a proliferation decreasing-effective amount of a pharmaceutical composition comprising at least one jasmonate ester of formula III, so as to decrease proliferation of said hyperproliferative benign epidermal cells:

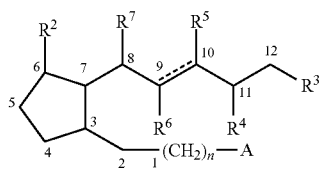
(III)

wherein

A is COR$^1$;

R$^1$ is quinolinyloxy;

R$^2$ is selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, OR$^8$, oxo and NR$^{9a}$R$^{9b}$;

R$^3$, R$^4$, R$^5$, R$^6$ and R$^7$ are each independently selected from the group consisting of hydrogen, halogen, unsubstituted or substituted C$_1$-C$_{12}$ alkyl, unsubstituted or substituted C$_1$-C$_{12}$ haloalkyl, unsubstituted or substituted C$_3$-C$_8$ cycloalkyl, unsubstituted or substituted aryl, unsubstituted or substituted heteroaryl, OR$^8$ and NR$^{9a}$R$^{9b}$, or R$^5$ and R$^6$ together with the carbons to which they are attached form a C$_3$-C$_8$ cycloalkyl or a C$_3$-C$_8$ cycloalkyl substituted by halo;

or one of R$^5$ and R$^6$ represents an oxygen atom which is bonded to C$_6$, thereby forming an oxygen-containing 6 or 5 membered heterocyclic ring, respectively;

wherein the bond between C$_9$ and C$_{10}$ can be a single or double bond;

R$^8$, R$^{9a}$ and R$^{9b}$ are each independently selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, glucosyl, or R$^{9a}$ and R$^{9b}$ can together with the nitrogen to which they are attached form an unsubstituted or substituted heterocyclic or heteroaromatic ring optionally containing one or more additional heteroatom selected from O, N and S; and n is selected from 0, 1 and 2;

including salts, hydrates, solvates, polymorphs, optical isomers, geometrical isomers, enantiomers, diastereomers, and mixtures thereof.

13. The method according to claim 12, wherein the quinolinyloxy is unsubstituted or substituted with one or more alkyl groups.

14. The method according to claim 12, wherein R$^2$ is oxo.

15. The method according to claim 12, wherein the bond between C$_9$ and C$_{10}$ is a double bond, and R$^3$, R$^4$, R$^5$, R$^6$ and R$^7$ are each hydrogen.

16. The method according to claim 12, wherein the bond between C$_9$ and C$_{10}$ is a single bond, and R$^3$, R$^4$, R$^5$, R$^6$ and R$^7$ are each hydrogen.

17. The method according to claim 12, wherein the jasmonate ester is represented by the structure of formula C:

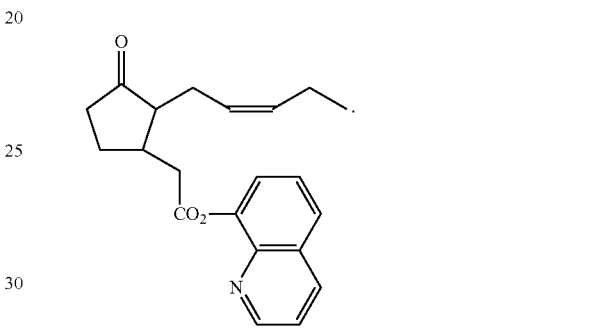

18. The method according to claim 12, wherein the composition is formulated for topical administration.

19. The method according to claim 18, wherein the composition is in a form selected from the group consisting of an ointment, a cream a lotion, a foam and a gel.

* * * * *

UNITED STATES PATENT AND TRADEMARK OFFICE
CERTIFICATE OF CORRECTION

PATENT NO. : 9,284,252 B2  
APPLICATION NO. : 14/497020  
DATED : March 15, 2016  
INVENTOR(S) : Max Herzberg and Frederic Revah It is certified that error appears in the above-identified patent and that said Letters Patent is hereby corrected as shown below:

On the title page of the patent, please change Assignee from "SEPAL PHARMA, LTD., Sitrya, (IL)" to --RAMOT AT TEL-AVIV UNIVERSITY LTD., Tel Aviv (IL)--.

Signed and Sealed this
Twenty-eighth Day of June, 2016

Michelle K. Lee
*Director of the United States Patent and Trademark Office*